United States Patent
Weaver et al.

(10) Patent No.: US 10,486,139 B2
(45) Date of Patent: Nov. 26, 2019

(54) IRO$_2$ CATALYSTS AND METHODS OF USE THEREOF

(71) Applicant: University of Florida Research Foundation, Inc., Gainesville, FL (US)

(72) Inventors: Jason F. Weaver, Gainesville, FL (US); Tao Li, Gainesville, FL (US); Zhu Liang, Gainesville, FL (US)

(73) Assignee: UNIVERSITY OF FLORIDA RESEARCH FOUNDATION, INC., Gainesville, FL (US)

( * ) Notice: Subject to any disclaimer, the term of this patent is extended or adjusted under 35 U.S.C. 154(b) by 0 days.

(21) Appl. No.: 15/939,726

(22) Filed: Mar. 29, 2018

(65) Prior Publication Data

US 2018/0280938 A1 Oct. 4, 2018

Related U.S. Application Data

(60) Provisional application No. 62/479,081, filed on Mar. 30, 2017.

(51) Int. Cl.
| | | |
|---|---|---|
| C07C 2/00 | (2006.01) | |
| C07C 29/00 | (2006.01) | |
| C07C 45/00 | (2006.01) | |
| B01J 23/00 | (2006.01) | |
| B01J 37/00 | (2006.01) | |
| B01J 23/46 | (2006.01) | |
| B01J 37/14 | (2006.01) | |
| C07C 45/28 | (2006.01) | |
| C07C 29/48 | (2006.01) | |
| C07C 2/84 | (2006.01) | |
| B01J 35/00 | (2006.01) | |

(52) U.S. Cl.
CPC .......... *B01J 23/468* (2013.01); *B01J 35/002* (2013.01); *B01J 37/14* (2013.01); *C07C 2/84* (2013.01); *C07C 29/48* (2013.01); *C07C 45/28* (2013.01); *C07C 2523/46* (2013.01); *Y02P 20/52* (2015.11)

(58) Field of Classification Search
CPC . C07C 2/84; C07C 29/48; C07C 45/28; B01J 23/468; B01J 37/14
See application file for complete search history.

(56) References Cited

U.S. PATENT DOCUMENTS

| | | |
|---|---|---|
| 4,443,647 A | 4/1984 | Jones et al. |
| 2013/0211137 A1 | 8/2013 | Basset et al. |

FOREIGN PATENT DOCUMENTS

| | | |
|---|---|---|
| WO | 2014025274 | 2/2014 |
| WO | 2014073995 | 5/2014 |
| WO | 2017027755 | 2/2017 |

OTHER PUBLICATIONS

R. Horn, Methane activation by heterogeneous catalysis. Catal. Lett. 145, 23-39 (2015).
W. Taifan, CH4 conversion to value added products: Potential, limitations and extensions of a single step heterogeneous catalysis. Appl. Catal., B 198, 525-547 (2016).
J. F. Weaver, The adsorption and reaction of low molecular weight alkanes on metallic single crystal surfaces. Surf. Sci. Rep. 50, 107-199 (2003).
T. S. Wiltrig, The interaction of ethane, propane, isobutane, and neopentane with the (110) surface of iridium. J. Chem. Phys. 76, 3305-3315 (1982).
P. D. Szuromi, Adsorption and reaction of n-alkanes on the Pt(110)-(1×2) surface. J. Phys. Chem. 89, 2497-2502 (1985).
C. B. Mullins, Trapping-mediated dissociative chernisorption of ethane on Ir(110)-(1×2). J. Chem. Phys. 92, 4508-4512 (1990).
A. V. Hamza, The dynamics of the dissociative adsorption of alkanes on Ir(110). J. Chem. Phys. 86, 6506-6514 (1987).
C. T. Campbell, Enthalpies and entropies of adsorption on well-defined oxide surfaces: Experimental measurements. Chem, Rev, 113, 4106-4135 (2013).
E. W. McFarland, Catalysis by doped oxides. Chem. Rev. 113, 4391-4427 (2013).
L. Chen, Adsorption of small hydrocarbons on rutile TiO2(110). Surf. Sci, 650, 83-92 (2016).
J. F. Weaver, Alkane activation on crystalline metal oxide surfaces. Chem. Soc. Rev. 43, 7536-7547 (2014).
J. F. Weaver, Surface chemistry of late transition metal oxides. Chem. Rev. 113, 4164-4215 (2013).
F. Zhang, Propane sigma-complexes on PdO(101): Spectroscopic evidence of the selective coordination and activation of primary C-H bonds. Angew. Chem., Int. Ed. 54, 13907-13911 (2015).
C. Hall, Transition metal alkane complexes, Chem. Rev. 96, 3125-3146 (1996).
N. M. Martin, Intrinsic ligand effect governing the catalytic activity of Pd oxide thin films. ACS Catal. 4, 3330-3334 (2014).
C. C. Wang, C-H bond activation of methane via sigma-d interaction on the IrO2(110) surface: Density functional theory study. J. Phys. Chem. C 116, 6367-6370 (2012).
A. Antony, PhD Dissertation, University of Florida, Gainesville, FL (2013).
T. L. M. Pharn, Ethylene formation by methane dehydrogenation and C-C coupling reaction on a stoichiometric IrO2 (110) surface—a density functional theor investigation, Catal. Sci. Techno.l 5, 4064-4071 (2015).
T. Li, Adsorption of alkanes on stoichiometric and oxygen-rich RuO2( 110). Phys. Chem. Chem. Phys. 18, 22647-22660 (2016).
T. Li, Adsorption and Oxidation of n-Butane on the Stoichiometric RuO2(110) Surface. J. Phys. Chem. C 120, 9863-9873 (2016).
B. A. Arndtsen, Unusually mild and selective hydrocarbon C-H bond activation with positively charged indium(III) complexes. Science 270, 1970-1973 (1995).

(Continued)

*Primary Examiner* — Sikarl A Witherspoon
(74) *Attorney, Agent, or Firm* — Thomas | Horstemeyer, LLP; Christopher B. Linder

(57) ABSTRACT

Embodiments of the present disclosure provide for IrO$_2$ catalysts, methods of making IrO$_2$ catalysts, methods of using IrO$_2$ catalysts to make methanol, formaldehyde, and/or ethylene from CH$_4$, systems for using IrO$_2$ catalysts, and the like.

16 Claims, 11 Drawing Sheets

(56) References Cited

OTHER PUBLICATIONS

C. T. Reeves, Low transiational energy mechanisms in the dissociative chemisorption of methane on iridium and platinum surfaces. J. Mol. Catal, A: Chem. 167, 207-215 (2001).

Y. B. He, Oxidation of Ir(111): From O-Ir-O trilayer to bulk oxide formation. J. Phys. Chem. C 112, 11946-11953 (2008).

W. H. Chung, Surface oxides of Ir(111) prepared by gas-phase oxygen atoms, Surf. Sci. 606, 1965-1971 (2012).

R. Rai, Growth and termination of an IrO2(100) film on Ir(111). Surf. Sci, 252, 213-221 (2016).

C. T. Rettner, Role of surface-temperature in the precursor-mediated dissociative chemisorption of N2 on W(100). Phys. Rev. Lett. 61, 966-989 (1988).

S. Grimme, A consistent and accurate ab initio parametrization of density functional dispersion correction (DFT-D) for the 94 elements H-Pu. J. Chem. Phys. 132, 154104 (2010).

K. Anic, CO adsorption on reconstructed Ir(100) surfaces from UHV to mbar pressure: A LEED, TPD, and PM-IRAS study. J. Phys. Chem. C 120, 10838-10848 (2016).

G. Kisters, Adsorption of CO on the unreconstructed and reconstructed Ir(100) surface. Surf. Sci, 245, 65-71 (1991).

T. J. Lerotholi, Phase mixing and phase separation accompanying the catalytic oxidation of CO on Ir(100). Surf. Sc. 601, 1285-1295 (2007).

P. E. Blochl, Projector augmented-wave method. Phys. Rev. B 50, 17953-17979 (1994).

G. Kresse, J. Hafner, Ab initio Hellmann-Feynman molecular dynamics for liquid metals. J. Non-Cryst. Solids 156, 956-960 (1993).

G. Kresse, Ab initio molecular dynamics for liquid metals. J. Non-Cryst. Solids 193, 222-229 (1995).

J. P. Perdew, Generalized gradient approximation made simple. Phys. Rev. Lett. 77, 3865-3868 (1996).

G. Henkelman, A climbing image nudged elastic band method for finding saddle points and minimum energy paths, J. Chem. Phys. 113, 9901-9904 (2000).

H. Over, Surface chemistry of ruthenium dioxide in heterogeneous catalysis and electrocatalysis: From fundamental to applied research. Chem. Rev. 112, 3356-3426 (2012).

A. Lobo, Interaction of H2O with the RuO2(110) surface studied by HREELS and TDS. Surf. Sci. 523, 279-286 (2003).

B. Hammer, Improved adsorption energetics within density-functional theory using revised Perdew-Burke-Ernzerhof functionals. Phys. Rev. B 59, 7413-7421 (1999).

K. Lee, Higher-accuracy van der Waals density functional. Phys. Rev. B 82, (2010).

S. Gautier, Molecular adsorption at Pt(111). How accurate are DFT functionals? Phys. Chem, Chem. Phys. 17, 28921-28930 (2015).

K. Momma, F. Izumi, VESTA 3 for three-dimensional visualization of crystal, volumetric and morphology data. J. Appl. Crystallogr. 44, 1272-1276 (2011).

Thong Le Minh Pham; A DFT Study of Ethane Activation on IrO2 Surface by Precursor-mediated Mechanism, Apr. 2017, ResearchGate, 8-14.

F. Cavani, Oxidative dehydrogenation of ethane and propane: How far from commercial implementation? Dipartimento di Chimica Industriale e dei Materiali, Alma Mater Studiorum Univesita'di Bologna, Viale Risorgimento 4, 40136 Bologna, Italy1 Available online Jul. 2, 2007.

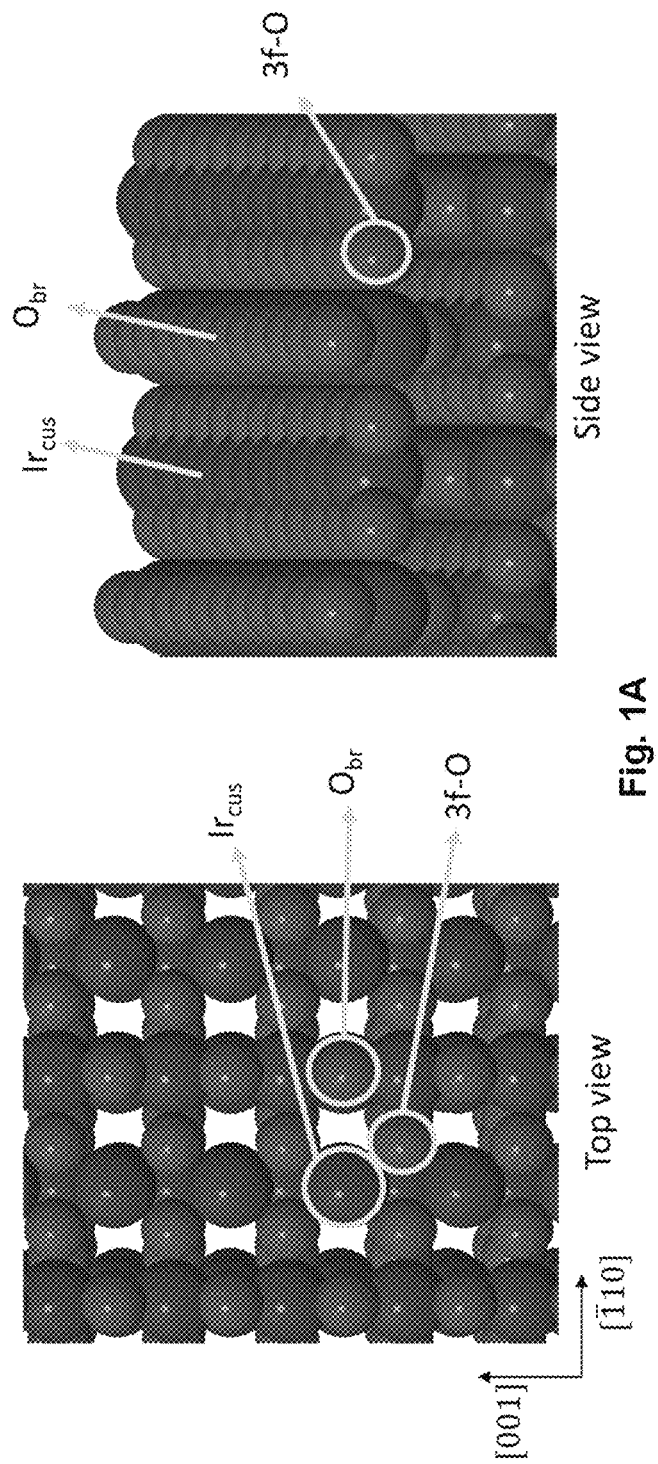
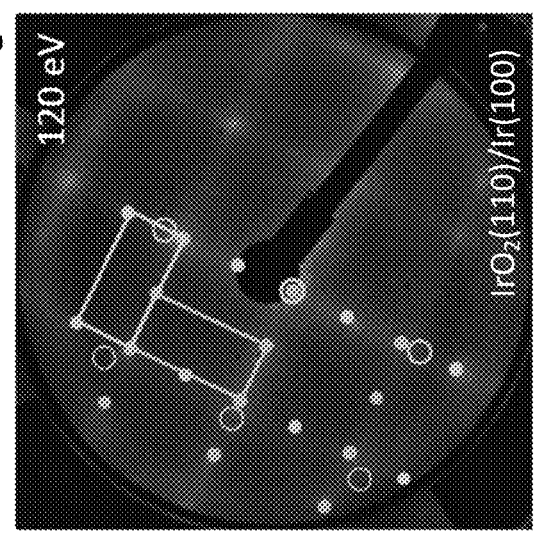
Fig. 1A
Fig. 1B

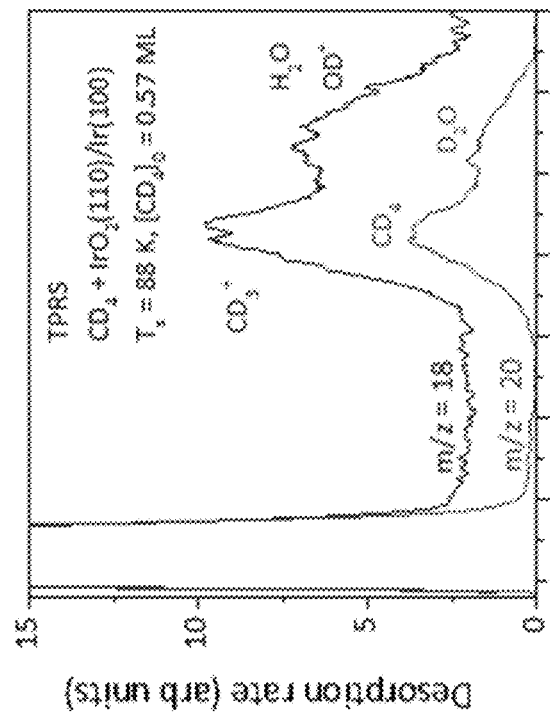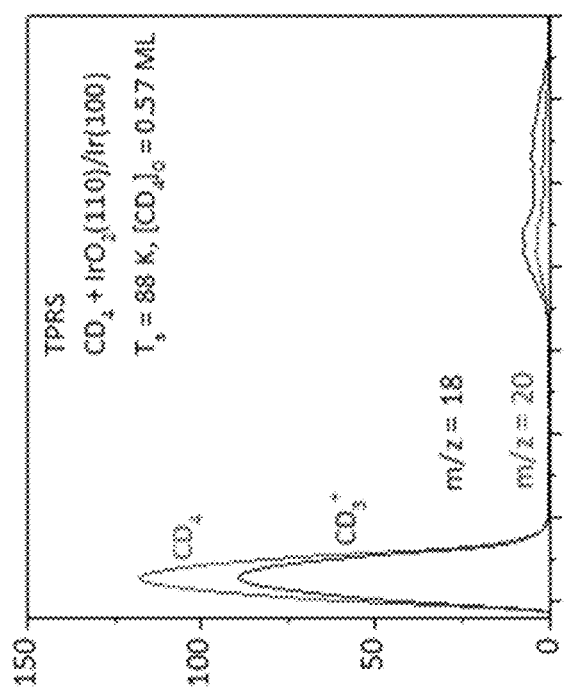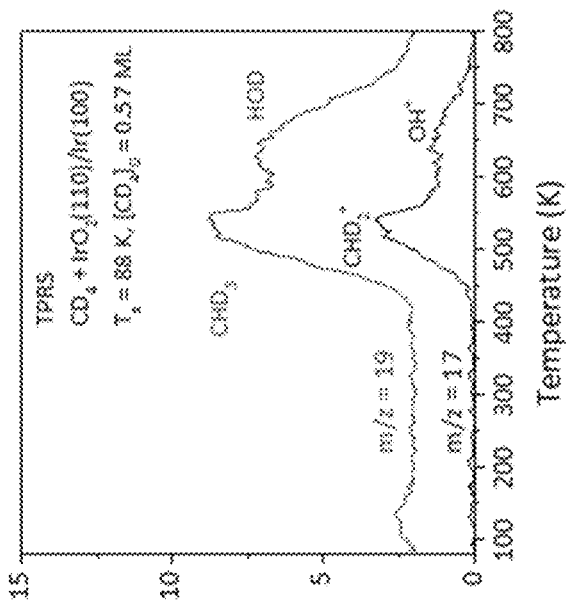
Fig. 7A
Fig. 7B
Fig. 7C

IRO₂ CATALYSTS AND METHODS OF USE THEREOF

CROSS-REFERENCE TO RELATED APPLICATIONS

This application claims the benefit of and priority to U.S. Provisional Application Ser. No. 62/479,081, having the title "METHANE ACTIVATION ON THE $IrO_2(110)$ SURFACE", filed on Mar. 30, 2017, the disclosure of which is incorporated herein by reference in its entirety.

BACKGROUND

The increasing supply of natural gas provides substantial motivation for developing catalytic processes that can efficiently and directly transform methane ($CH_4$) to value-added products such as methanol, formaldehyde, or ethylene. Selective catalytic transformations of $CH_4$ remains a major challenge in catalysis.

SUMMARY

Embodiments of the present disclosure provide for $IrO_2$ catalysts, methods of making $IrO_2$ catalysts, methods of using $IrO_2$ catalysts to make methanol, formaldehyde, and/or ethylene from $CH_4$, systems for using $IrO_2$ catalysts, and the like.

In an aspect, the present disclosure provides for a catalyst comprising: a $IrO_2(110)$ substrate having a rutile $IrO_2(110)$ surface having exposed cus-Ir atom sites. In an embodiment, the stoichiometric termination of rutile $IrO_2(110)$ has a rectangular unit cell with dimensions of 3.16×6.36 Å with the corresponding lattice vectors aligned along the [001] and [110] crystallographic directions, respectively.

In an aspect, the present disclosure provides for a method of making an $IrO_2(110)$ surface, comprising: oxidizing Ir(100) substrate at about 725 K to 875K and a $O_2$ partial pressure of about 0.5 to 100 Torr; evacuating $O_2$ from the chamber until the pressure reaches less than $10^{-7}$ Torr with the sample held at 600 to 650 K; and forming a rutile $IrO_2(110)$ surface having exposed cus-Ir atom sites.

In an aspect, the present disclosure provides for a method of making a product from $CH_4$, comprising: exposing a catalyst comprising an $IrO_2$ substrate having a rutile $IrO_2$ (110) surface having exposed cus-Ir atom sites and a $CH_4$ gas to one another; and forming one or more products. In an aspect, the products can include $CH_3OH$, $CH_2O$, $C_2H_4$, or a combination thereof.

In an aspect, the present disclosure provides for a system of activating $CH_4$, comprising: a first device for introducing $CH_4$ to a catalyst comprising an $IrO_2$ substrate having a rutile $IrO_2(110)$ surface having exposed cus-Ir atom sites; a second device for collecting one or more products of the catalytic reaction of $CH_4$.

BRIEF DESCRIPTION OF THE DRAWINGS

Further aspects of the present disclosure will be more readily appreciated upon review of the detailed description of its various embodiments, described below, when taken in conjunction with the accompanying drawings.

FIGS. 1A-B provide example characterizations of the $IrO_2(110)$ surface.

FIG. 3A shows reaction yield vs. $CH_4$ exposure to $IrO_2(110)$ for different surface temperatures. FIG. 3B provides the initial dissociation probability vs. surface temperature and FIG. 3C is an Arrhenius plot as discussed in the text.

FIGS. 7A-C provide examples of adsorption and reaction of $CD_4$ on $IrO_2(110)$.

Figure 2B:
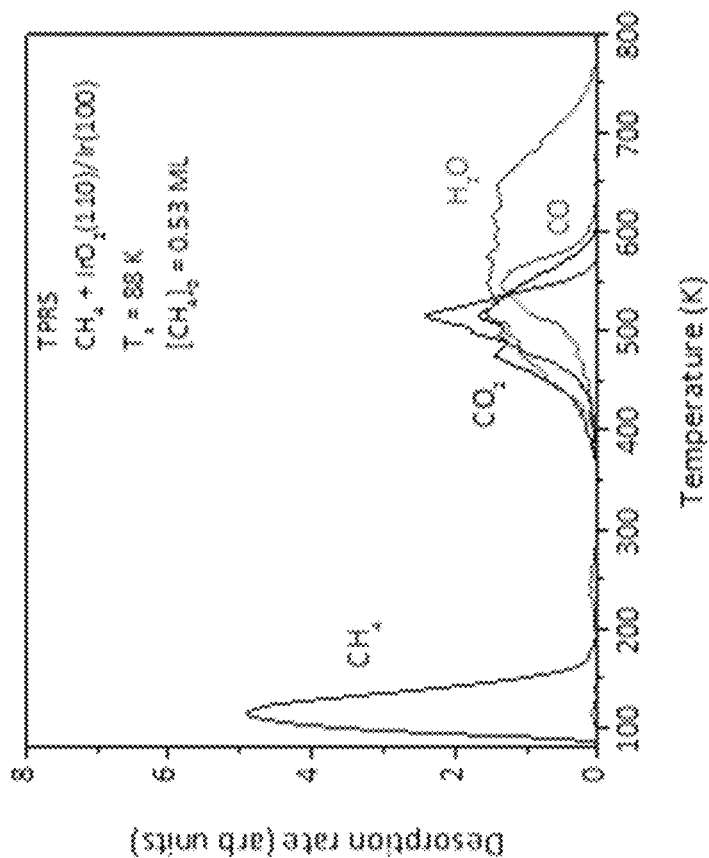
FIGS. 2A-B are examples of TPRS spectra showing the adsorption and reaction of $CH_4$ on $IrO_2(110)$. TPRS yields are shown in FIGS. 2C-2D.

The drawings illustrate only example embodiments and are therefore not to be considered limiting of the scope described herein, as other equally effective embodiments are within the scope and spirit of this disclosure.

DETAILED DESCRIPTION

Before the present disclosure is described in greater detail, it is to be understood that this disclosure is not limited to particular embodiments described, as such may, of course, vary. It is also to be understood that the terminology used herein is for the purpose of describing particular embodiments only, and is not intended to be limiting, since the scope of the present disclosure will be limited only by the appended claims.

Where a range of values is provided, it is understood that each intervening value, to the tenth of the unit of the lower limit (unless the context clearly dictates otherwise), between the upper and lower limit of that range, and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of chemistry, inorganic chemistry, material science, and the like, which are within the skill of the art. Such techniques are explained fully in the literature.

The following examples are put forth so as to provide those of ordinary skill in the art with a complete disclosure and description of how to perform the methods and use the compositions and compounds disclosed and claimed herein. Efforts have been made to ensure accuracy with respect to numbers (e.g., amounts, temperature, etc.), but some errors and deviations should be accounted for. Unless indicated otherwise, parts are parts by weight, temperature is in ° C., and pressure is in atmosphere. Standard temperature and pressure are defined as 25° C. and 1 atmosphere.

Before the embodiments of the present disclosure are described in detail, it is to be understood that, unless otherwise indicated, the present disclosure is not limited to particular materials, reagents, reaction materials, manufacturing processes, or the like, as such can vary. It is also to be understood that the terminology used herein is for purposes of describing particular embodiments only, and is not intended to be limiting. It is also possible in the present disclosure that steps can be executed in different sequence where this is logically possible.

It must be noted that, as used in the specification and the appended claims, the singular forms "a," "an," and "the" include plural referents unless the context clearly dictates otherwise. Thus, for example, reference to "a support" includes a plurality of supports. In this specification and in the claims that follow, reference will be made to a number of terms that shall be defined to have the following meanings unless a contrary intention is apparent.

Discussion

Embodiments of the present disclosure provide for $IrO_2$ catalysts, methods of making $IrO_2$ catalysts, methods of using $IrO_2$ catalysts to make methanol, formaldehyde, and/or ethylene from $CH_4$, systems for using $IrO_2$ catalysts, and the like. $IrO_2$ catalyst of the present disclosure are advantageous because they facilitate the adsorption and C—H bond activation of $CH_4$. $CH_4$ readily undergoes C—H bond cleavage on the $IrO_2$ catalyst (e.g., $IrO_2(110)$ surface) at temperatures of about 150 K. The initial dissociation of $CH_4$ on $IrO_2$ catalyst occurs through a precursor-mediated process where the activation energy for initial C—H bond cleavage is 9.5 kJ/mol lower than the binding energy of the molecularly adsorbed precursor.

In an aspect, the present disclosure provides for a $IrO_2$ catalyst having a $IrO_2(110)$ substrate having a rutile $IrO_2$ (110) surface having exposed cus-Ir atom sites. The stoichiometric termination of rutile $IrO_2(110)$ has a rectangular unit cell with dimensions of about 3.16×6.36 Å with the corresponding lattice vectors aligned along the [001] and [110] crystallographic directions. Rows of cus-Ir atoms ($Ir_{cus}$) are separated by rows of bridging-O atoms ($O_{br}$) that run parallel to the [001] direction. The $Ir_{cus}$ and $O_{br}$ atoms each lack a bonding partner compared with the bulk and expose single coordination vacancies. Based the $IrO_2(110)$ unit cell, the areal densities of $Ir_{cus}$ atoms and $O_{br}$ atoms would each equal to about 34 to 40, about 37%, or 37% of the surface atom density of Ir(100). Because the cus-metal atoms are active adsorption sites, adsorbate coverages were specified in units of ML (monolayer), where 1 ML is equal to the density of $Ir_{cus}$ atoms on the $IrO_2(110)$ surface.

In an aspect, the $IrO_2$ catalyst can be a layer on another substrate or can be the substrate itself. The $IrO_2$ catalyst can be a particle having dimensions in the micrometer to nanometer range and can have regular (e.g., spherical) or irregular shapes. In embodiments where the $IrO_2$ catalyst is a layer, the layer can be of a thickness sufficient to achieve activation of the C—H bonds and can be in the monolayer to nanometer range or more.

In an embodiment of the present disclosure, the $IrO_2$ catalyst can be made by oxidizing an Ir(100) substrate at about 725 to 875 K and a $O_2$ partial pressure of about 0.5 to 100 Torr for a time period of about 5 to 20 minutes. The $O_2$ gas is subsequently evacuated from the reaction vessel with the sample held at a temperature between 600 and 650 K. After the pressure falls below $10^{-7}$ Torr, the reactive $IrO_2$ (110) layer may be cooled to lower temperature to preserve the reactive cus-surface sites. Additional details are provided in Example 1.

The $IrO_2$ catalyst can be used to produce desired products due to its ability to activate C—H bonds in $CH_4$. In an aspect, the method of making a product from $CH_4$ can include exposing the $IrO_2$ catalyst comprising an $IrO_2$ substrate having a rutile $IrO_2(110)$ surface having exposed cus-Ir atom sites and a $CH_4$ gas to one another, where the catalytic reaction of the gas with the $IrO_2$ catalyst forms one or more products. The products formed can include: $CH_3OH$, $CH_2O$, $C_2H_4$, and a combination thereof.

A system can be used to conduct the catalytic reaction of the $IrO_2$ catalyst and the $CH_4$ gas. The system can include a first device (e.g., a reaction chamber made of a material such as stainless steel) that can include the $IrO_2$ catalyst. The temperature and pressure of the reaction chamber can be controlled using known vacuum systems and temperature control systems. The $CH_4$ gas can be introduced to the reaction chamber and the temperature and the pressure can be adjusted to produce desired product(s) (e.g., $CH_3OH$, $CH_2O$, $C_2H_4$, and a combination thereof). The $CH_4$ readily undergoes C—H bond cleavage on the $IrO_2(110)$ surface through a precursor-mediated process. Additional reactants can be added before, during and/or after the catalytic reaction to produce the desired product(s). The system includes a second device (e.g., another chamber made of a material such as stainless steel or other appropriate material) that is part of or interfaced with the first device to separate, remove, or capture the desired product(s) using known vacuum technologies, gas separation or capture technologies, and the like. Once the desired product(s) are obtained, they can be appropriately processed for future use. The system can be configured to process $CH_4$ gas in a systematic manner that maximizes the life of the $IrO_2$ catalyst.

EXAMPLES

Now having described the embodiments of the disclosure, in general, the examples describe some additional embodiments. While embodiments of the present disclosure are described in connection with the example and the corresponding text and figures, there is no intent to limit embodiments of the disclosure to these descriptions. On the contrary, the intent is to cover all alternatives, modifications, and equivalents included within the spirit and scope of embodiments of the present disclosure.

Example 1

A limitation with most existing heterogeneous catalysts is that initial C—H bond cleavage is rate-controlling, so subsequent reaction steps occur rapidly and are difficult to control. Achieving $CH_4$ activation at low temperature could eliminate this limitation and allow for its selective oxidation.

However, catalytic materials that can readily activate $CH_4$ at low temperatures (e.g., below 300 K) have not been reported.

The activation of light alkanes on solid surfaces can occur by direct and precursor-mediated mechanisms. In the direct mechanism, the alkane molecule undergoes C—H bond cleavage during its initial collision with the surface and reaction is activated with respect to the gas-phase energy level. In the precursor-mediated mechanism, the alkane first adsorbs intact on the surface and the resulting molecularly adsorbed state serves as a precursor for C—H bond cleavage. Dissociation by the precursor-mediated mechanism is facile when the activation energy for C—H bond cleavage ($E_r$) is smaller than the activation energy for desorption ($E_d$) of the molecularly adsorbed precursor. Molecular beam experiments show that $CH_4$ dissociation is activated ($E_r > E_d$) on the many crystalline transition-metal surfaces that have been investigated. Facile dissociation ($E_r < E_d$) of $CH_4$ on a solid surface has not been previously reported, but other light alkanes do undergo facile activation on certain facets of metallic Ir and Pt. Prior studies also report only weak molecular adsorption of alkanes on many metal oxides, including alkaline-earth oxides, rare-earth oxides and $TiO_2$.

Previous studies indicate that specific facets of late transition-metal (TM) oxides, in particular PdO(101), can promote alkane C—H bond cleavage (11, 12). The key aspect of these surfaces is the presence of pairs of coordinatively unsaturated (cus) metal and oxygen atoms on the surface that promote the formation and facile C—H bond cleavage of adsorbed alkane σ-complexes (11). The cus-Pd sites of PdO(101) datively bond with alkanes (11-13), and that the resulting molecularly-adsorbed species are analogous to coordination compounds known as alkane σ-complexes (14). The dative interaction with cus-metal sites facilitates alkane activation by both strengthening the alkane-surface binding as well as weakening the Pd-coordinated C—H bonds. The cus-oxygen atoms also play a central role in alkane C—H bond cleavage on PdO(101) by acting as H-atom acceptors. In situ measurements show that formation of a PdO(101) layer gives rise to high rates of $CH_4$ oxidation over Pd surfaces under steady-state conditions at elevated pressure, thus demonstrating that fundamental studies with PdO(101) are directly relevant for understanding $CH_4$ oxidation over Pd surfaces under realistic conditions (15).

Density functional theory (DFT) calculations predict that small alkanes also form strongly-bound σ-complexes on rutile $RuO_2$ and $IrO_2$ surfaces (11, 16-20). The formation of alkane σ-complexes on $RuO_2$(110) has been confirmed, and it has also been shown that n-butane undergoes facile C—H bond cleavage during temperature-programmed reaction spectroscopy (TPRS) experiments in ultrahigh vacuum (UHV) (19, 20). Dispersion-corrected DFT calculations predict that the binding energy of the $CH_4$ σ-complex on $IrO_2$(110) is greater by about 40 kJ/mol than the energy barrier for C—H bond cleavage, so that $CH_4$ activation should occur at high rates on $IrO_2$(110) at temperatures as low as 100 K (17, 18).

The facile activation of $CH_4$ by the $IrO_2$(110) surface reinforces earlier studies which show that iridium possesses an unusual ability to activate hydrocarbon C—H bonds. As originally reported by Ardntsen and Bergman (21), cationic Ir(III) complexes are among the most highly reactive transition-metal compounds known for promoting C—H bond activation. Further, crystalline surfaces of metallic Ir exhibit the highest activity toward alkane C—H bond cleavage among the metal surfaces that have been investigated, and the presence of low coordination surface sites strongly enhances the reactivity of Ir and other metals toward alkane activation. A common feature among these systems is the availability of coordinatively-unsaturated Ir centers to bind and activate adsorbed alkanes.

Experimental reports of the growth and surface chemistry of crystalline $IrO_2$ are sparse because well-defined $IrO_2$ surfaces are challenging to prepare for fundamental UHV studies. At the $O_2$ partial pressures typically used in UHV experiments, oxygen adsorption on crystalline Ir surfaces reaches an effective saturation at submonolayer O-atom coverages (~0.50 ML) because kinetic limitations suppress more extensive oxygen uptake. An in situ surface x-ray diffraction study shows that relatively thick layers of rutile $IrO_2$, exposing (110) and (100) facets, can form during Ir(111) oxidation but only when the $O_2$ partial pressure and temperature are >100 mbar and 775 K (23). Oxidation of Ir(111) with plasma-generated oxygen beams can produce multilayer $IrO_2$ structures under UHV conditions (24, 25). Rai et al. reported that a high-quality $IrO_2$(100) layer forms during Ir(111) oxidation with gaseous O-atoms, with the oxide saturating at a thickness of about four layers for growth temperatures below ~650 K (25). However, the $IrO_2$(100) layer was completely oxygen-terminated, so this surface would be chemically inactive for $CH_4$ reactions at moderate temperature. Thus, the formation of relatively thick, rutile $IrO_2$(110) surfaces via metallic Ir oxidation that expose cus-Ir sites occurs only at sufficiently high temperature and requires relatively high oxidant fluxes.

In the present disclosure, investigations included the adsorption and C—H bond activation of $CH_4$ on a high-quality $IrO_2$(110) layer that was grown by oxidizing Ir(100) at 775 K and an $O_2$ partial pressure of 5 Torr. It is shown herein that $CH_4$ readily undergoes C—H bond cleavage on the $IrO_2$(110) surface at temperatures down to at least 150 K. Analysis of temperature-dependent rate data shows that the initial dissociation of $CH_4$ on $IrO_2$(110) occurs through a precursor-mediated process wherein the activation energy for initial C—H bond cleavage is 9.5 kJ/mol lower than the binding energy of the molecularly adsorbed precursor.

The stoichiometric termination of rutile $IrO_2$(110) has a rectangular unit cell with dimensions of (3.16×6.36 Å) with the corresponding lattice vectors aligned along the [001] and [110] crystallographic directions, respectively (FIG. 1A). Rows of cus-Ir atoms ($Ir_{cus}$) are separated by rows of bridging-O atoms ($O_{br}$) that run parallel to the [001] direction. The $Ir_{cus}$ and $O_{br}$ atoms each lack a bonding partner compared with the bulk and expose single coordination vacancies. Based the $IrO_2$(110) unit cell, the areal densities of $Ir_{cus}$ atoms and $O_{br}$ atoms would each equal to 37% of the surface atom density of Ir(100). Because the cus-metal atoms are active adsorption sites, adsorbate coverages were specified in units of ML (monolayer), where 1 ML is equal to the density of $Ir_{cus}$ atoms on the $IrO_2$(110) surface.

Model representations of the stoichiometric $IrO_2$(110) surface with $Ir_{cus}$, $O_{br}$ and 3f-O atoms labeled are shown in FIG. 1A. The Ir and O atoms are represented as blue and red spheres, respectively. FIG. 1B provides a LEED pattern obtained from an ~3.5 nm $IrO_2$(110) film grown on Ir(100) by oxidizing in 5 Torr of $O_2$ at 775 K. The orange circles mark the LEED spot positions from the Ir(100) substrate and the light blue and pink spots represent reciprocal space points computed for two orientations of the rectangular $IrO_2$(110) unit cell with dimensions of 1.16 a×2.34 a where a is the Ir(100) lattice constant.

Figure 5B:
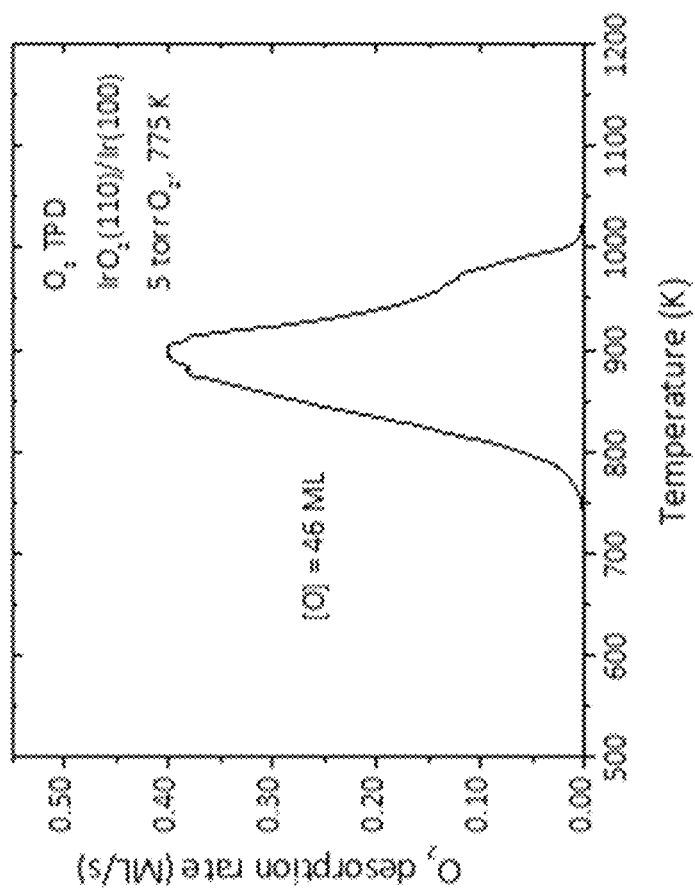
FIGS. 5A-B provide an estimation of $IrO_2(110)$ film thickness.
Figure 5A:
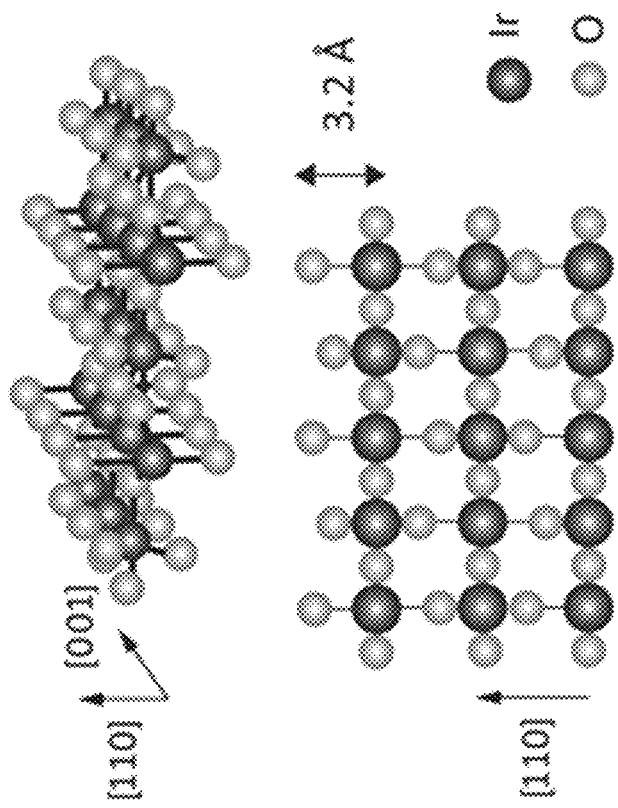
Figures 6A, 6B:
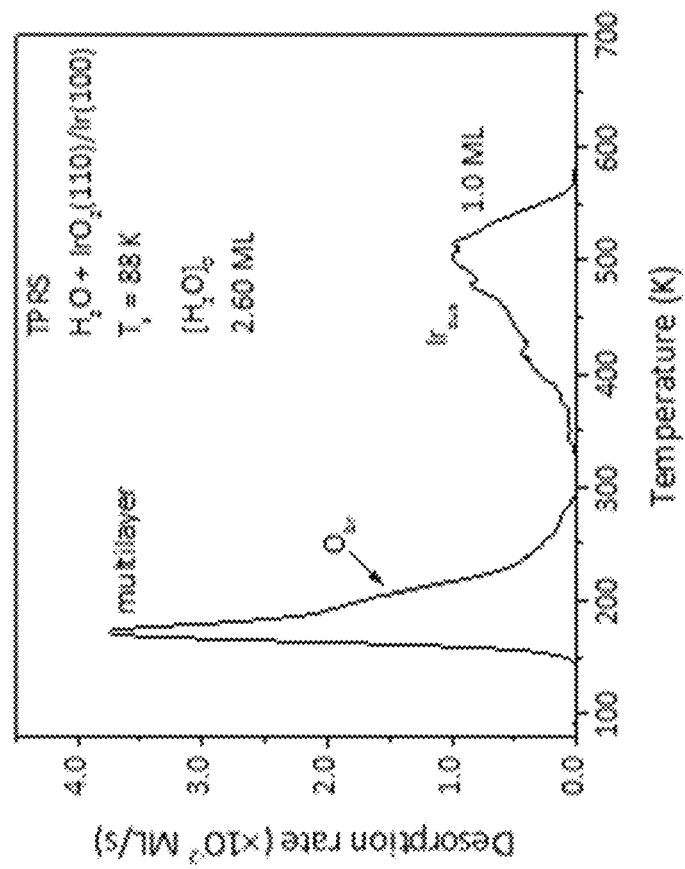
FIGS. 6A-B provide examples of adsorption of $O_2$ and $H_2O$ on $IrO_2(110)$. The TPD spectrum of $O_2$ (FIG. 6A) and $H_2O$ (FIG. 6B) was taken after exposing the $IrO_2(110)$ film to 10 L $O_2$ and 1.5 L $H_2O$ at 88 K, respectively.

Oxidation of Ir(100) at 775 K and an $O_2$ partial pressure of 5 Torr produced a high-quality $IrO_2$(110) layer that exposed the stoichiometric termination. The experimental methods used herein are described in the Materials and Methods section. A representative LEED pattern obtained after oxidizing Ir(100) to form the $IrO_2(110)$ layer (FIG. 1B) agreed quantitatively with that simulated for two rotational domains of the $IrO_2(110)$ structure with unit cell dimensions of 3.16 Å by 6.36 Å. The $IrO_2(110)$ lattice vectors align with the high-symmetry [001] and [110] directions of the Ir(100) growth substrate. The absence of Ir(100) diffraction spots in the LEED pattern is consistent with the presence of a conformal $IrO_2(110)$ layer that is thick enough to completely attenuate the elastic scattering of electrons from the underlying Ir(100) substrate. The $IrO_2(110)$ layer is stable to a temperature of ~725 K but thermally decomposes at higher temperature. Quantification of the $O_2$ TPD feature centered at ~900 K (FIGS. 5AB) allows an estimate that the $IrO_2(110)$ film contained 46 ML of O-atoms and was ~3.5 nm thick. FIG. 5A provides schematic models of the $IrO_2(110)$ layer. Perspective view (top) and layer stacking along the [110] direction (bottom) are both shown. Each layer consists of 2 ML Ir and 4 ML O atoms where 1 ML is equal to the cus-Ir density. FIG. 5B is an $O_2$ TPD spectrum obtained by thermally decomposing the $IrO_2(110)$ layer in UHV. It was confirmed that the $IrO_2(110)$ layer was stoichiometrically terminated by using TPRS to characterize the adsorption behavior of $O_2$ and $H_2O$ (FIGS. 6A-B).

Figure 2A:
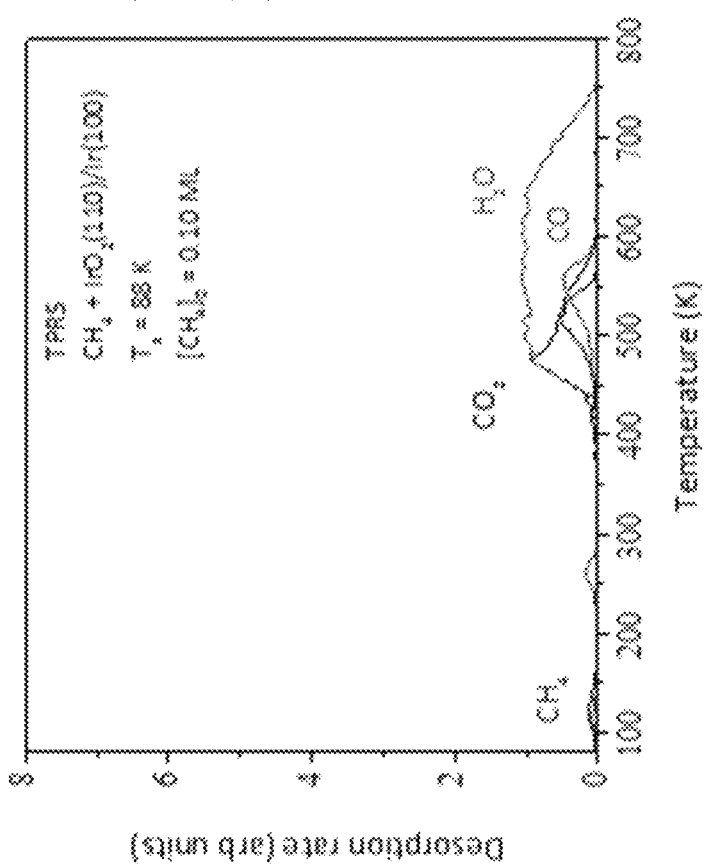

The TPRS traces obtained after adsorbing low and high $CH_4$ coverages (0.10 and 0.53 ML, FIGS. 2A and 2B) on the $IrO_2(110)$ surface at 88 K revealed that a large fraction of the adsorbed $CH_4$ oxidizes to CO, $CO_2$, and $H_2O$ during heating, with the CO and $CO_2$ products desorbing between ~400 and 600 K. The small CO TPRS feature near 250 K is consistent with a small quantity of CO that adsorbed from the vacuum background. The $H_2O$ TPRS feature is broader than the CO and $CO_2$ features and spanned a range from ~400 to 750 K. Desorption of $CH_4$ also occurred with separate TPRS peaks centered at ~130 K and 515 K. The low-temperature TPRS peak is characteristic of the desorption of a $CH_4$ σ-complex that is bound strongly to the $IrO_2(110)$ surface (~34 to 43 kJ/mol). FIGS. 2A-B show TPRS spectra of $CH_4$, $H_2O$, CO and $CO_2$ obtained after adsorbing $CH_4$ on $IrO_2(110)$ at 88 K to generate coverages of 0.10 ML (FIG. 2A) and 0.53 ML (FIG. 2B). In contrast, Redhead analysis of the high-temperature $CH_4$ peak suggests an activation energy for desorption (130-140 kJ/mol) that is far too high for this TPRS peak to originate from molecularly adsorbed $CH_4$. The high temperature $CH_4$ peak results from the recombination of adsorbed $CH_3$ groups and H atoms were confirmed by performing experiments of $CD_4$ adsorption onto an as-prepared $IrO_2(110)$ film that was covered by a small amount of residual H-atoms (see SM for details). Based on the detected mass fragments, these measurements demonstrate that only $CD_4$ desorbs in the TPRS peak at 130 K while both $CD_4$ and $CD_3H$ contribute to the TPRS peak at 510 K (FIGS. 7A-C). FIGS. 7A-B show TPRS spectra of $CD_4^+$ (m/z=20) and $CD_3^+$ (m/z=18), and FIG. 7C is a TPRS spectra of $CHD_3^+$ (m/z=19) and $CHD_2^+$ (m/z=17) obtained after adsorbing $CD_4$ on $IrO_2(110)$ at 88 K. The high temperature shoulder (575 K to 800 K) of each spectrum are water product/fragment, which are labeled based on their m/z ratios. Below, it is shown that energies derived from DFT calculations also support the described assignments of the low and high temperature $CH_4$ TPRS peaks to molecular vs. recombinative desorption processes.

The TPRS data demonstrates that a large quantity of $CH_4$ undergoes C—H bond activation on the $IrO_2(110)$ surface, with the dissociated products oxidizing to CO, $CO_2$ and $H_2O$ and also recombining to $CH_4$ at higher temperature. The observed reactivity is consistent with a precursor-mediated mechanism wherein a fraction of the adsorbed $CH_4$ σ-complexes undergo C—H bond cleavage rather than desorbing, and the resulting $CH_3$ and OH fragments react during continued heating. An implication is that $CH_4$ C—H bond cleavage occurred readily on $IrO_2(110)$ at temperatures as low as ~150 K and even lower, i.e., below the temperatures at which the adsorbed complexes desorb during TPRS. There are no other known materials that exhibit such high activity toward promoting $CH_4$ C—H bond cleavage.

Figures 2C, 2D:
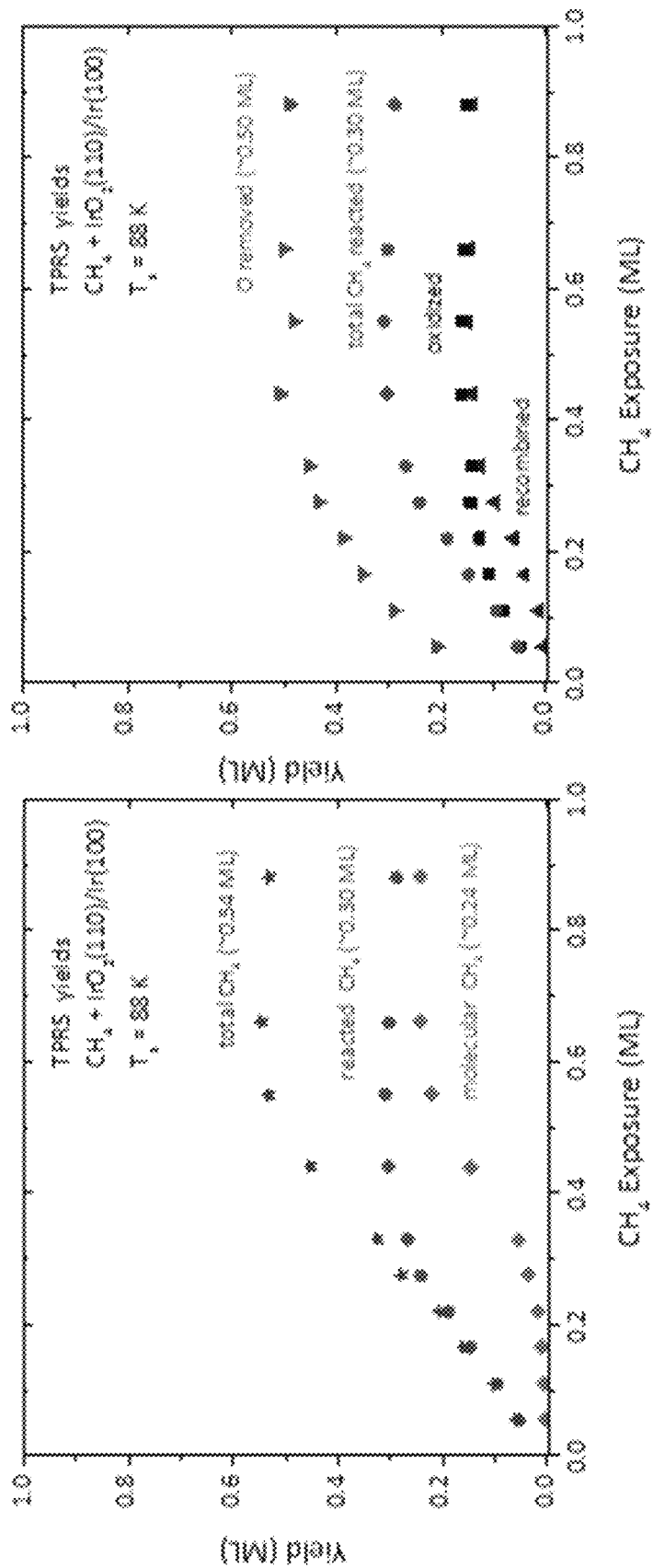

The TPRS yields of reacted vs. unreacted $CH_4$ on $IrO_2$(110) as a function of the $CH_4$ exposure performed at 88 K are shown in FIG. 2C. The yield of reacted $CH_4$ is defined here as the sum of the yields of CO, $CO_2$ and $CH_4$ that desorbed in the TPRS peak at ~515 K, which are attributed to recombinatively desorbed $CH_4$, and the yield of unreacted $CH_4$ ("molecular") as equal to the amount of $CH_4$ that desorbed in the low temperature TPRS peak. The yield of reacted $CH_4$ increased as the exposure initially increased, while the yield of unreacted $CH_4$ remained quite low. More than 85% of the adsorbed $CH_4$ reacted during TPRS at total $CH_4$ coverages below ~0.30 ML. The yield of reacted $CH_4$ plateaued at ~0.30 ML after ~1.0 ML exposure. The yield of unreacted $CH_4$ increased only after the yield of reacted $CH_4$ had nearly saturated, demonstrating that the $IrO_2(110)$ surface is highly reactive toward $CH_4$ at $CH_4$ coverages below about 0.33 ML. The total $CH_4$ coverage saturated at a value near 0.54 ML. A similar saturation coverage of $CH_4$ on the $RuO_2(110)$ surface at 80 K has been reported in previous research (19). Thus, ~55% of the adsorbed $CH_4$ on $IrO_2(110)$ reacted during TPRS when the $CH_4$ layer is saturated. The large quantity of $CH_4$ that reacts during TPRS is consistent with C—H bond activation occurring on the $Ir_{cus}$ and $O_{br}$ sites that are present on the crystalline terraces of the $IrO_2(110)$ surface. TPRS yields of molecularly desorbed and reacted methane and the total $CH_4$ TPRS yield as a function of the $CH_4$ exposure to the surface are shown in FIG. 2C. The total yield of reacted $CH_4$, yields of oxidized $CH_4$ (CO+$CO_2$) and recombinatively-desorbed $CH_4$ and the total amount of O-atoms removed from the oxide during TPRS as a function of the $CH_4$ exposure is shown in FIG. 2D.

The change in TPRS yields of reaction products with $CH_4$ exposure are shown in FIG. 2D. Dissociated $CH_4$ preferentially oxidized to CO and $CO_2$ during TPRS for initial $CH_4$ coverages below ~0.16 ML, but the selectivity toward oxidation over recombination continuously decreased as the total reaction yield increased. The oxidized and recombined yields became equal at ~0.16 ML when the total reaction yield reached saturation at 0.30 ML. The $CO_2$ yield was ~1.4 times higher than the CO yield at all $CH_4$ coverages, with yields reaching saturation values of 0.09 and 0.065 ML. Lastly, $CH_4$ oxidation during TPRS removed ~0.50 ML of O-atoms from the $IrO_2(110)$ surface when the yield of oxidized products saturated, which is equal to half of the $O_{br}$ site concentration. The stoichiometric constraints as well as a relatively high stability of $HO_{br}$ groups likely play an important role in determining the total reaction yield as well as the branching between $CH_4$ oxidation and recombination during TPRS.

Experimental estimates of the $CH_4$ dissociation probability obtained as a function of the surface temperature were evaluated using a kinetic model for the precursor-mediated dissociation of $CH_4$. The dissociation of an alkane from a molecularly-adsorbed precursor state was represented by the following kinetic scheme (3, 6).

$$RH(g) \underset{k_d}{\overset{\xi F}{\rightleftharpoons}} RH(ad) \overset{k_r}{\longrightarrow} R(ad) + H(ad) \qquad (1)$$

where RH represents an alkane molecule, ξ is the probability for molecular adsorption, F is the incident flux of gaseous RH at the surface, and $k_d$ and $k_r$ are rate coefficients for desorption and dissociation ("reaction") via C—H bond cleavage of the molecularly-adsorbed RH σ-complex. The kinetic scheme treats the reaction step as irreversible and is applicable at a temperature below that at which recombination becomes kinetically relevant. It is assumed that the probability for $CH_4$ to adsorb molecularly into the σ-complex state is unity and independent of the surface temperature, because molecular adsorption is non-activated and the impingent $CH_4$ molecules have kinetic energies that are much lower than the strength of the molecule-surface interaction (~2.5 vs. 40 kJ/mol) (3). Molecular beam scattering experiments show that probabilities for non-activated adsorption are nearly independent of the surface temperature (26). The following expression for the dissociative chemisorption probability in the limit of zero coverage ($S_0$) was derived by applying the steady-state approximation to the rate of formation of molecularly-adsorbed alkanes:

$$S_0 = \frac{\xi k_r}{k_r + k_d} \qquad (2)$$

If it is assumed that the Arrhenius equation describes the temperature dependence of each rate coefficient, then:

$$\ln\left(\frac{\xi}{S_0} - 1\right) = \ln\left(\frac{v_d}{v_r}\right) - \frac{(E_d - E_r)}{RT_s} \qquad (3)$$

where $v_j$ and $E_j$ represent the prefactor and activation energy for reaction j, and $T_s$ is the surface temperature. Thus, if $CH_4$ dissociates on $IrO_2(110)$ by a precursor-mediated mechanism, then a plot of $$\ln\left(\frac{\xi}{S_0} - 1\right) \text{ vs. } \frac{1}{T_s}$$

will be linear and the Arrhenius construction will provide values for the apparent pre-factor $$\frac{v_r}{v_d}$$

and activation energy $E_r - E_d$ for initial C—H bond cleavage. To obtain estimates of the $CH_4$ dissociation probability, the TPRS yields of reacted $CH_4$ (CO, $CO_2$, and recombinatively desorbed $CH_4$) was measured as a function of the $CH_4$ exposure at several fixed surface temperatures between 175 and 300 K. 175 K was selected as the lower limit because this temperature lies above the trailing edge of the low-temperature $CH_4$ TPD peak. Because molecularly adsorbed $CH_4$ accumulates negligibly above 175 K, the TPRS yields of CO, $CO_2$, and recombinatively-desorbed $CH_4$ were equal to the amount of $CH_4$ that dissociated on the surface during the $CH_4$ exposures. 300 K was selected as the upper limit to minimize the loss of surface oxygen via product desorption and thus avoid possible changes in surface reactivity that could occur during the $CH_4$ exposures caused by partial reduction of the oxide surface. The TPRS results also showed that recombination of CHs and H atoms was negligible below 300 K and could be ignored in the analysis.

Figure 3A:
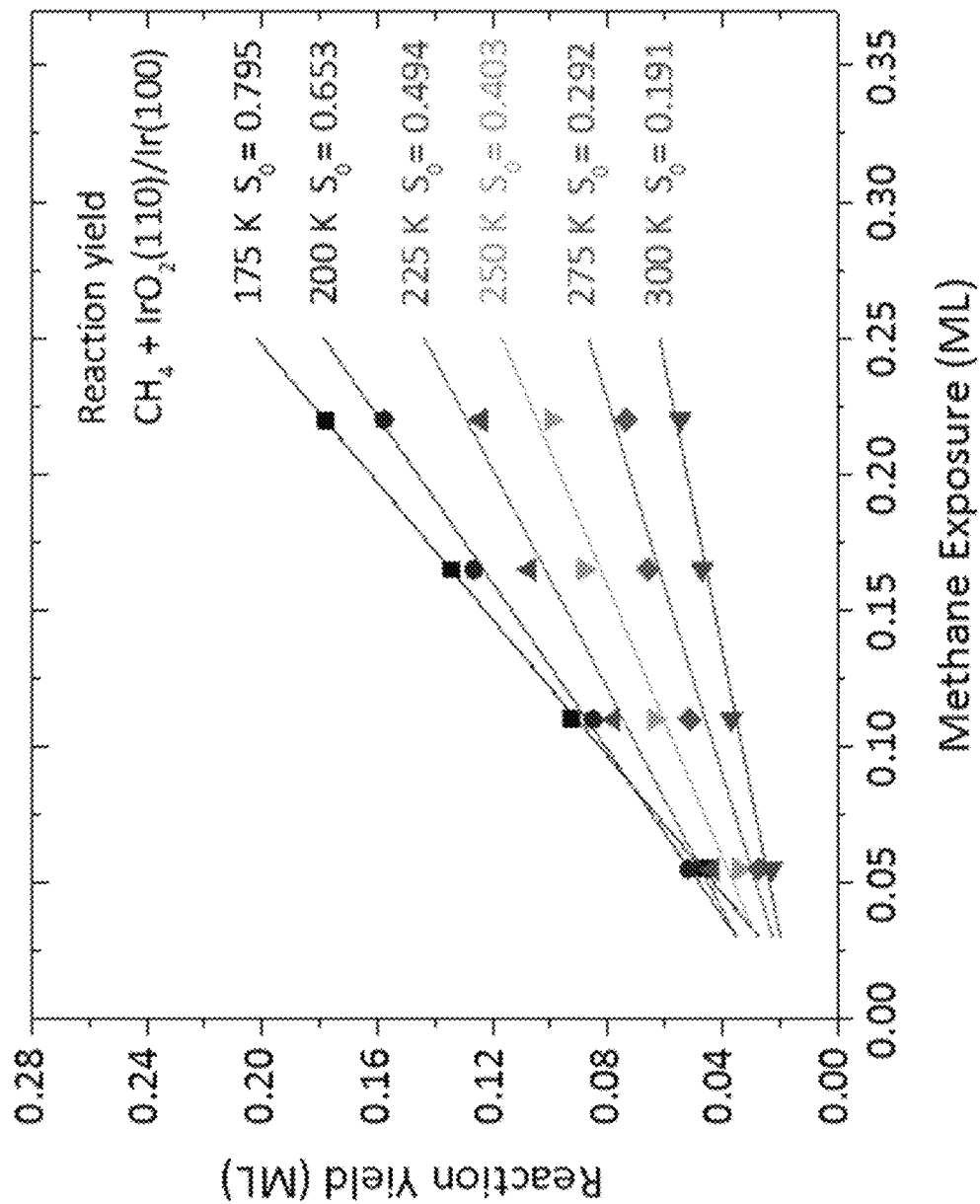
FIGS. 3A-C are examples of kinetic analysis of $CH_4$ dissociation on the $IrO_2(110)$ surface.
Figure 3B:
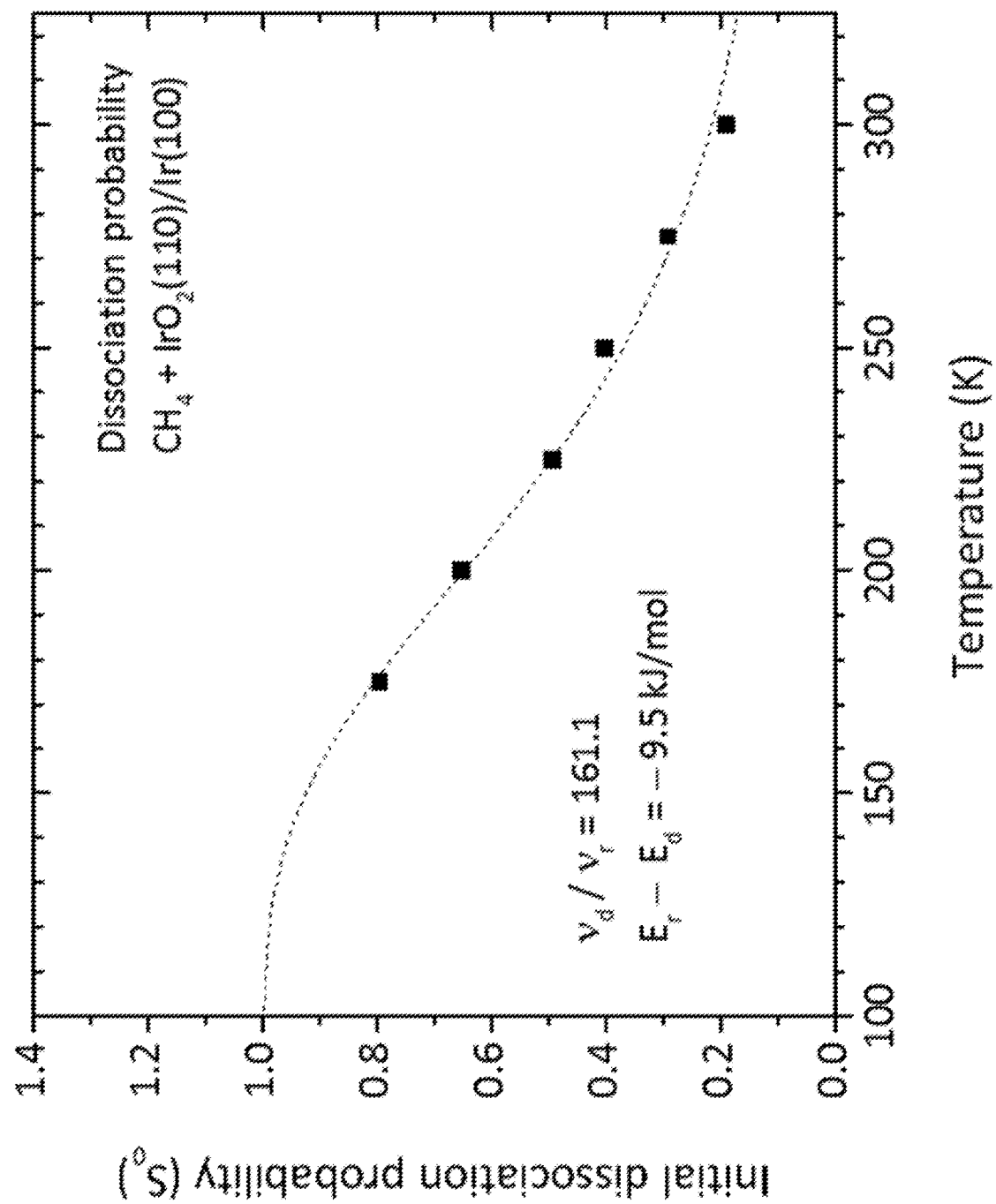

$CH_4$ reaction yields were measured as a function of the exposure at several $T_s$; exposures were short to maintain low coverages of the reaction products. Each isotherm of the reaction yield vs. exposure (FIG. 3A) was well-approximated as linear, with the slopes decreasing with increasing $T_s$. The linear behavior was expected because the probability for dissociative chemisorption is approximately independent of the adsorbate coverage at low coverage. In this limit, the coverage of dissociated $CH_4$ [R] is given by the equation, $[R] = S_0 Ft$ where the $CH_4$ exposure is equal to the product of the exposure time t and the incident flux F, which was estimated as $1.1 \times 10^{-2}$ ML/s. The slope of the initial portion of an isotherm is thus equal to the initial dissociation probability of $CH_4$ on $IrO_2(110)$ for the $T_s$ at which the exposure was conducted. Our estimates of the initial dissociation probability $S_0$ at various $T_s$ of $CH_4$ on $IrO_2(110)$ are plotted in FIG. 3B along with the curve that represents the expression $S_0(T_s)$ determined from our kinetic analysis, as discussed below. The initial dissociation probability decreased from about 80% to 19% with increasing $T_s$ from 175 to 300 K. The $IrO_2(110)$ surface was remarkably active toward promoting C—H bond cleavage: 80% of the $CH_4$ molecules that collide with the clean surface underwent C—H bond scission at a surface temperature of only 175 K. The decrease in initial dissociation probability with increasing $T_s$ is characteristic of a facile precursor-mediated mechanism.

The excellent linear fit of $$\ln\left(\frac{\xi}{S_0} - 1\right) \text{ vs. } \frac{1}{T_s}$$

Figure 3C:
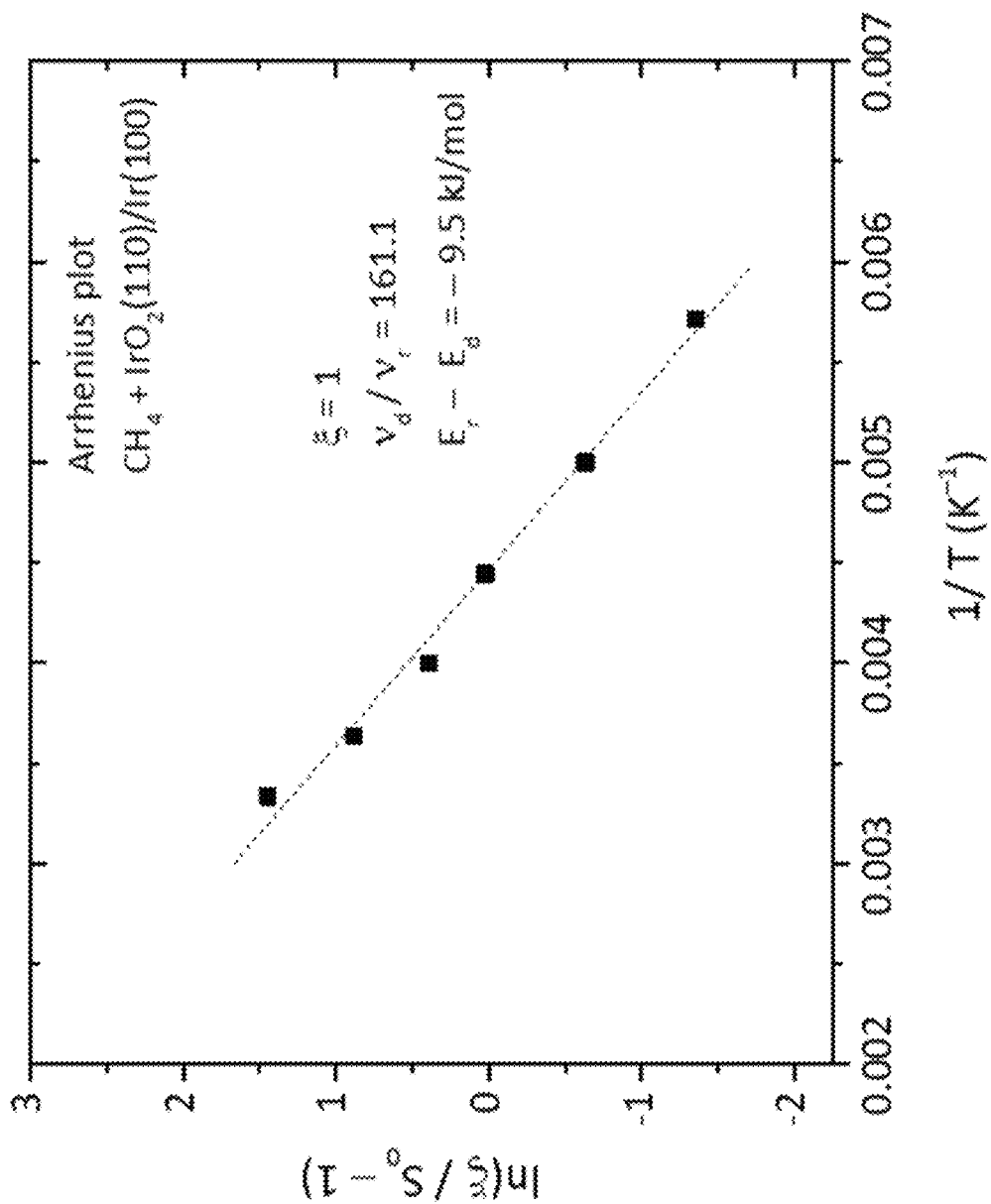

(FIG. 3C) further supports the conclusion that $CH_4$ dissociation on $IrO_2(110)$ occurs by a precursor-mediated mechanism, with an apparent pre-factor of $6.2 \times 10^{-3}$ and an activation energy of −9.5 kJ/mol (negative relative to the gas-phase reference). It is noted that the apparent activation energy and pre-factor for reaction depend only weakly on the value of ξ used in the analysis. Analysis of the low temperature $CH_4$ TPRS peak suggests a binding energy of ~38 kJ/mol at low $CH_4$ coverage, from which a value of 28.5 kJ/mol for the activation energy of C—H bond cleavage of the $CH_4$ σ-complex on $IrO_2(110)$ can be estimated. For comparison, the reaction barrier that was estimated for $CH_4$ activation on $IrO_2(110)$ is roughly half of that for $CH_4$ activation on PdO(101) (28.5 vs. 56 kJ/mol).

Figure 4:
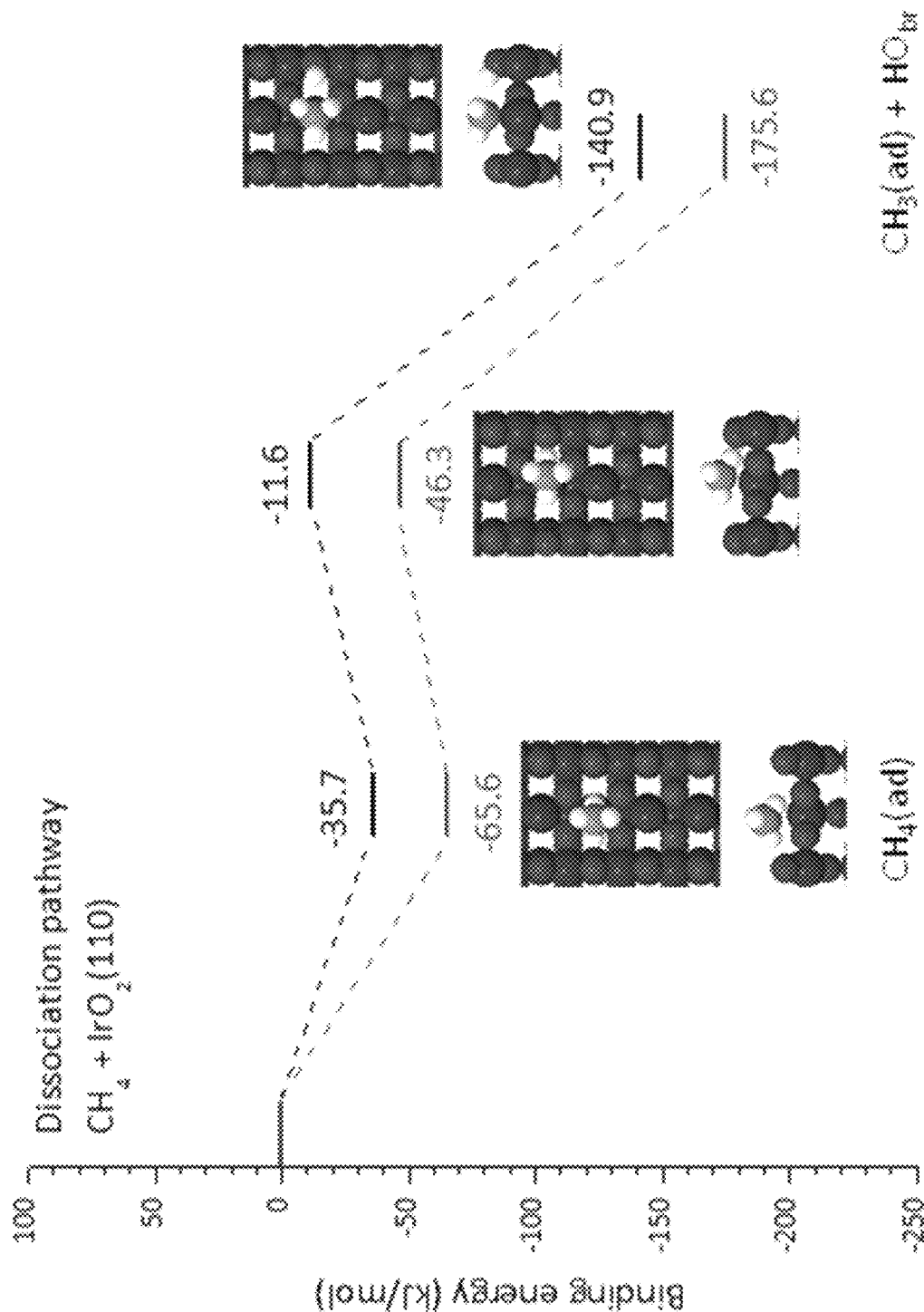
FIG. 4 provides example energy diagrams for the formation and C—H bond cleavage of a $CH_4$ σ-complex on $IrO_2(110)$.
Figure 8:
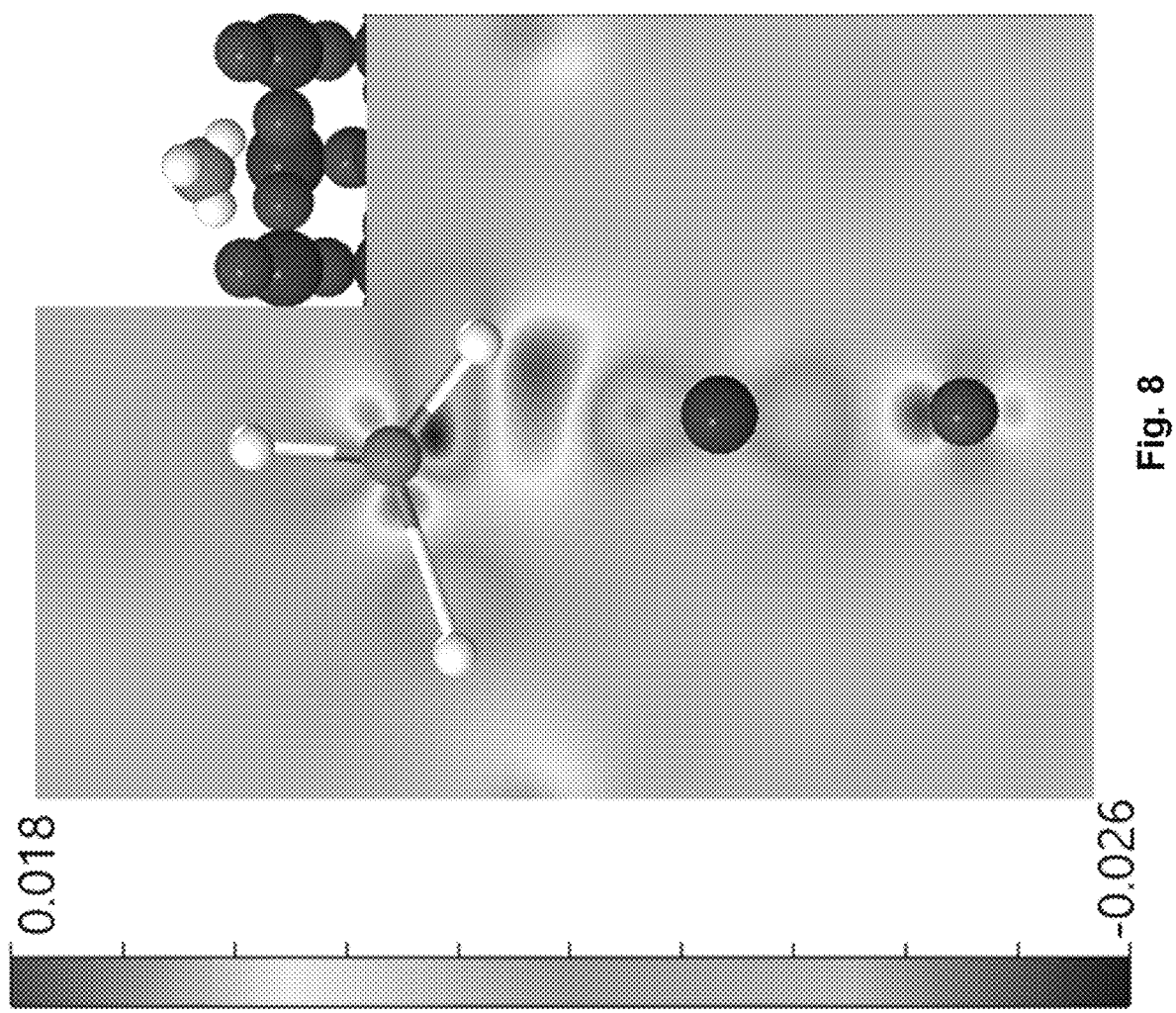
FIG. 8 is an example of a charge-density difference plot (electrons/bohr³) for the $\eta^2$ $CH_4$ σ-complex on $IrO_2(110)$ predicted using DFT-PBE viewed along the [001] direction.

The energy diagrams were computed for the formation and dissociation of a $CH_4$ σ-complex on $IrO_2(110)$ as well as images of the initial, transition and final states are shown in FIG. 4. The shown results were computed using conventional DFT (black) and DFT-D3 (red) as well as images of the initial, transition and final states. The energies were determined using conventional DFT and the dispersion-corrected DFT-D3 method (27), both employing the PBE exchange-correlation functional. Details of the DFT calculations can be found in the Materials and Methods below, along with $CH_4$ adsorption energies obtained using several DFT functionals that incorporate dispersion. The calculations predict a facile pathway for C—H bond cleavage of $CH_4$ on $IrO_2(110)$. A plot of the charge-density difference (FIG. 8) shows that the $CH_4$ molecule forms a strongly-bound σ-complex on $IrO_2(110)$ by adopting an $\eta^2$ configuration and datively bonding with a single $Ir_{cus}$ atom. The image was generated using VESTA (41) and shows the CH4 molecule, an Ircus atom and an O-atom underneath the Ircus atom. The inset shows a representation of the $CH_4/IrO_2(110)$ structure. Back donation of charge from the $Ir_{cus}$ atom to $CH_4$ weakens the C—H bond and promotes C—H bond cleavage. In the C—H bond cleavage step, the $CH_4$ complex transfers an H-atom to a neighboring $O_{br}$ atom, resulting in $CH_3$—$Ir_{cus}$ and $HO_{br}$ moieties. Both the DFT and DFT-D3 calculations predict that the energy barrier for dissociation lies below the gas-phase energy level so that C—H bond cleavage is energetically preferred over desorption of the adsorbed $CH_4$ complex.

The dispersion-correction included in the DFT-D3 calculations increased the binding energies computed for each adsorbed state compared with the results of the DFT-PBE calculations. Because the enhancement is similar for the initial state and the transition state, both the DFT and DFT-D3 calculations predict similar values for the C—H bond cleavage barrier relative to the initial adsorbed state ($E_r$~19 vs. 24 kJ/mol), where these values agreed reasonably well with the value of $E_r$=28.5 kJ/mol estimated from our experimental data. Also, our experimental estimates of the binding energy and apparent dissociation barrier for the adsorbed $CH_4$ complex agreed well with the values computed using DFT-PBE. From the experimental data, values of $E_d$~38 kJ/mol and $E_r-E_d$=−9.5 kJ/mol were estimated, where these values agree to within better than 2.5 kJ/mol of the values predicted by DFT-PBE ($E_d$=35.7 kJ/mol; $E_r-E_d$=−11.6 kJ/mol). The rate coefficient governing the recombinative desorption of $CH_4$ via the reaction $CH_3$+$HO_{br}$→$CH_4(g)$+$O_{br}$ is approximately equal to the rate coefficient for only the recombination step that produces the adsorbed $CH_4$ σ-complex when the temperature is sufficiently high. The results of both the DFT-PBE and DFT-D3 calculations predict an energy barrier of about 129 kJ/mol for this recombination step (FIG. 4). For desorption pre-factors of $10^{12}$ and $10^{13}$ s$^{-1}$, the $CH_4$ TPRS peak observed at 515 K likely corresponds to activation energies of 130 and 140 kJ/mol, respectively.

The facile activation of $CH_4$ on cus-Ir/O surface pairs may provide opportunities for developing catalysts and catalytic processes that can promote efficient and selective methane functionalization. For example, certain co-reactants may directly react with $CH_4$-derived fragments on $IrO_2(110)$ to produce value-added compounds. It may also be possible to modify the $IrO_2(110)$ surface to limit its oxidizing power and/or incorporate cus-Ir/O surface pairs into other materials that promote more desirable methane chemistries, such as conversion to organic oxygenates or higher hydrocarbons.

Materials and Methods
Experimental Setup for UHV Surface Analysis Chamber (27) (27)

Experiments for this study were performed in an apparatus consisting of an UHV surface analysis chamber with an isolatable reaction cell that is attached to the bottom of the chamber. The UHV chamber contains a four-grid retarding field analyzer for surface characterization using low energy electron diffraction (LEED) and Auger electron spectroscopy (AES) and a shielded quadrupole mass spectrometer used for TPRS. The Ir(100) crystal employed in this study is a circular disk (9 mm×1 mm) that is attached to a liquid-nitrogen cooled, copper sample holder by 0.015" W wires that are secured to the edge of crystal. A type K thermocouple was spot-welded to the backside of the crystal for temperature measurements. Resistive heating, controlled using a PID controller that varies the output of a programmable DC power supply, supports linearly ramping from 80 K to 1500 K or maintaining the sample temperature. Sample cleaning consisted of cycles of Ar$^+$ sputtering (2000 eV, 15 mA) at 1000 K, followed by annealing at 1500 K for several minutes. The sample was subsequently exposed to 5×10$^{-7}$ Torr of $O_2$ at 900 K to remove surface carbon, followed by flashing to 1500 K to remove final traces of oxygen. The Ir(100) sample was considered to be clean when a sharp (5×1) LEED pattern was obtained consistent with the surface reconstruction of clean Ir(100), no impurities were detected using AES and negligible CO and $CO_2$ production was observed during flash desorption after adsorbing oxygen.

Experimental Setup for Ambient-pressure Reaction Cell $IrO_2(110)$ films were generated by oxidizing Ir(100) in the isolated reaction cell at an $O_2$ partial pressure of 5 Torr and a surface temperature of 775 K. The reaction cell is a six-way cross that is separated from the UHV chamber by a gate valve and a differentially-pumped tube that contains two spring-loaded Teflon sliding seals positioned at the top and bottom of the tube. The sample holder mounts onto the bottom of a well-polished stainless steel tube with a cross-sectional area that is larger than the holder. As the sample is translated downward into the reaction cell, the sliding seals grip the sample probe tube and establish seals that isolate the reaction cell from the UHV chamber. This sealing mechanism allows exposure of the Ir(100) sample to elevated gas pressures in the reaction cell at variable sample temperatures, while maintaining UHV in the analysis chamber. After completing the desired $O_2$ exposure, the reaction cell was evacuated and the sample translated back to the UHV chamber for surface characterization. The as-prepared $IrO_2$(110) film contains a small quantity (<0.10 ML) of H-atoms that likely adsorbed from the background in the reaction cell after the high-pressure $O_2$ exposure. The concentration of residual H-atoms was estimated by saturating the as-prepared oxide surface with $O_2$ and monitoring the amount of $H_2O$ that desorbs during TPRS. The residual H-atoms can be removed by exposing the film to $O_2$ in the UHV chamber while cycling the surface temperature between 300 K and 650 K.

Temperature Programmed Reaction Spectroscopy (TPRS) Measurements

The reactivity of $CH_4$ (Airgas, 99.999%) on the s-$IrO_2$ (110) ("s=stoichiometric") surface was studied using TPRS. Methane was delivered to the sample from a calibrated beam doser at an incident flux of approximately 0.011 ML/s with the sample-to-doser distance set to about 15 mm to ensure uniform impingement of methane across the sample surface. TPRS spectra were collected after methane exposures by positioning the sample in front of a shielded mass spectrometer at a distance of about 5 mm and then heating at a constant rate of 1 K/s until the sample temperature reached 700 K. Initially, a wide range of desorbing species was monitored to identify the main products that are generated from reactions of methane on s-$IrO_2(110)$, and it was found that the only species desorbing from the $CH_4$-exposed s-$IrO_2(110)$ sample are methane, water, CO and $CO_2$. After each TPRS experiment, the surface was exposed to 24 L of $O_2$ supplied through a tube doser while cycling the surface temperature between 300 and 650 K. Consecutive TPRS experiments demonstrate that this surface cleaning/restoration procedure fully restores the surface reactivity toward $CH_4$. However, caution must be made when performing TPRS to temperatures higher than 725 K, which is the onset of oxide decomposition. The data shows that the surface reactivity diminishes after repeated $CH_4$ adsorption at 88 K and ramping the temperature to 800 K during the TPRS measurements, even when performing the surface cleaning/restoration treatment between experiments. Repeating the same $CH_4$ exposure on oxide films generated on different days gave identical CO and $CO_2$ desorption features in the TPRS data. Such behavior supports the idea that the activation of $CH_4$ occurs on terraces rather than defects, because the latter would likely exhibit variability in concentration and distribution and thus cause variations in the observed reactivity.

Measurement of Product Yields

Atomic oxygen coverages were estimated by scaling integrated $O_2$ TPD spectra with those obtained from a saturated (2×1) layer containing 0.50 ML of O-atoms, prepared by exposing the Ir(100)–(1×1) surface to $O_2$ in UHV (28). To estimate CO desorption yields, integrated CO desorption spectra were scaled by an integrated TPD spectrum collected from a saturated c(2×2) layer containing 0.50 ML of CO that were prepared by adsorbing CO to saturation on Ir(100)–(1×1) at 300 K (29, 30). TPRS experiments of CO oxidation on O-covered Ir(100) to estimate the $CO_2$ desorption yields were performed. In these experiments, $O_2$, $CO_2$ and CO TPRS spectra were collected after exposing a (2×1)–O layer to a saturation dose of CO and it was then assumed that the $CO_2$ TPRS yield is equal to the difference between the initial (0.50 ML) and final coverages of oxygen where the final oxygen coverage is determined from the $O_2$ TPRS yield. Lastly, the $H_2O$ and $CH_4$ TPRS yields were estimated by scaling the intensity-to-coverage conversion factors determined for CO, $CO_2$ and $O_2$ with relative sensitivity factors reported for the mass spectrometric detection of these gases.

Computational Details

All plane wave DFT calculations were performed using the projector augmented wave pseudopotentials (31) provided in the Vienna ab initio simulation package (VASP) (32, 33). The Ir 5d and 6s states are treated as valence electrons, but the adsorption minima for $CH_4$ on $IrO_2(110)$ have also been tested using a pseudopotential that includes the Ir 5s and 5p states as valence electrons and a negligible change in the adsorption energy found. The Perdew-Burke-Ernzerhof (PBE) exchange-correlation functional (34) was used with a plane wave expansion cutoff of 400 eV. Dispersion interactions are modeled using the DFT-D3 method developed by Grimme et al. (29). This method provides accurate estimates of the adsorption energies of n-alkanes on PdO(101) (11) and $RuO_2(110)$ (19) in comparison with TPD-derived values. The bulk structure of $IrO_2$ was generated by using the PBE functional and the lattice constants a and c are predicted to be 4.54 Å and 3.19 Å, respectively. These DFT results are consistent with experimental values of a=4.50 Å and c=3.15 Å (12). Based on the bulk structure from DFT-PBE, the $IrO_2(110)$ surface was generated to perform DFT-PBE and DFT+D3 calculations. Four layers were employed to model the $IrO_2(110)$ film, resulting in an ~12 Å thick slab. The bottom two layers are fixed, but all other lattice atoms are allowed to relax during the calculations until the forces are less than 0.03 eV/Å. A vacuum spacing of ~25 Å was included, which is sufficient to reduce the periodic interaction in the surface normal direction. In terms of system size, a 1×4 unit cell with a corresponding 4×2×1 Monkhorst-Pack k-point mesh is used.

In the present study, the binding energy, $E_b$, of an adsorbed $CH_4$ molecule on the surface is defined using the expression, $$E_b = (E_{CH_4} + E_{surf}) - E_{CH_4/surf} \quad (4)$$

where $E_{CH_4/surf}$ is the energy of the initial state containing the adsorbed $CH_4$ molecule, $E_{surf}$ is the energy of the bare surface, and $E_{CH_4}$ is the energy of an isolated $CH_4$ molecule in the gas phase. All reported binding energies are corrected for zero-point vibrational energy. From equation 4, a large positive value for the binding energy indicates a high stability of the adsorbed $CH_4$ molecule under consideration. Barriers of C—H bond cleavage of adsorbed $CH_4$ on the $IrO_2(110)$ surface were evaluated using the climbing nudged elastic band (cNEB) method (35). All of the calculations were performed for a single methane molecule adsorbed within the 1×4 surface model of $IrO_2(110)$, and corresponds to a methane coverage equal to 25% of the $Ir_{cus}$ density.

Thermal Decomposition of the $IrO_2(110)$ Film

FIG. 5A shows ball and stick models of rutile $IrO_2$ shown in a perspective view and also a side view perpendicular to the [110] direction. Each repeat unit of the oxide along the [110] direction contains 4 ML of oxygen atoms and the spacing between these $IrO_2(110)$ layers is equal to 3.2 Å. FIG. 5B shows an $O_2$ TPD spectrum obtained during thermal decomposition of the $IrO_2(110)$ film that was grown on Ir(100) by oxidizing in 5 Torr of $O_2$ at 775 K for a duration of 10 minutes. Decomposition of the $IrO_2(110)$ film produces an $O_2$ TPD feature centered at ~900 K. From quantification of the $O_2$ desorption yield, it is estimated that the $IrO_2(110)$ film contained 46 ML of oxygen atoms. This quantity of oxygen atoms corresponds to an $IrO_2(110)$ film thickness of 3.5 nm, based on the structure of rutile $IrO_2$ (FIG. 5A).

$O_2$ and $H_2O$ Adsorption on the $IrO_2(110)$ Film

FIG. 6A shows an $O_2$ TPD spectrum obtained after exposing the $IrO_2(110)$ film to a saturation dose of $O_2$ at a surface temperature of 88 K. The $O_2$ TPD trace exhibits an intense feature below 300 K as well as a broad feature centered at ~515 K that are consistent with the molecular desorption of $O_2$ and the recombination of O-atoms from the $Ir_{cus}$ sites of $IrO_2(110)$, respectively. Oxygen also dissociatively chemisorbs on the s-$RuO_2(110)$ surface and recombinatively desorbs in a TPD feature between ~300 and 500 K (36). It is estimated that a total of 0.70 ML of oxygen desorbs in the TPRS experiment, with ~0.38 ML desorbing in the high temperature peak. The total oxygen coverage is equal to a large fraction of the density of the $Ir_{cus}$ atoms on the s-$IrO_2(110)$ surface. The saturation coverage of oxygen on the $Ir_{cus}$ sites is likely to be less than 1 ML, given that the random adsorption of dimers on a line of sites reaches a theoretical jamming coverage of 0.86 ML.

FIG. 6B shows a $H_2O$ TPD spectrum obtained after adsorbing 2.6 ML of $H_2O$ on the $IrO_2(110)$ film at 88 K. The $H_2O$ desorption trace exhibits a broad feature centered at ~500 K and an intense peak at 170 K with a shoulder at ~200 K. An estimated 1.0 ML of water desorbs in the high temperature peak and this feature is attributed to $H_2O$ species that are adsorbed on the $Ir_{cus}$ sites of $IrO_2(110)$. The sharp peak at ~170 K arises from water adsorbed in a multilayer state and the shoulder at 200 K is consistent with $H_2O$ adsorbed on $O_{br}$ sites. The $H_2O$ TPD spectrum obtained from $IrO_2(110)$ is similar to that reported for water-covered $RuO2(110)$ (37). The adsorption behavior of $O_2$ and $H_2O$ provides additional evidence that the $IrO_2(110)$ film grown in the disclosed experiments is stoichiometrically-terminated.

Adsorption of $CD_4$ on the $IrO_2(110)$ Film

TPRS experiments were performed with adsorbed $CD_4$ to confirm that the low and high temperature TPRS peaks of methane originate from molecular vs. recombinative desorption processes. The reactivity of $CD_4$ was lower than $CH_4$ but the kinetic isotope effect is not further discussed in this study. FIGS. 7A-C show TPRS spectra of the 17 to 20 amu mass fragments obtained after saturating an as-prepared s-$IrO_2(110)$ film with $CD_4$ at 88 K where the as-prepared film was covered by between 0.05 to 0.10 ML of H-atoms that adsorbed from the background (see Materials and Methods). The mass fragments to specific methane-derived ions were assigned as follows: 17 amu ($CHD_2^+$), 18 amu ($CD_3^+$), 19 amu ($CD_3H^+$) and 20 amu ($CD_4^+$). The 20 amu fragment arises from $CD_4$ while the 17 and 19 amu fragments originate from partially hydrogenated methane. The 18 and 20 amu TPRS traces exhibit an intense peak at 128 K (FIG. 7A), consistent with molecularly-adsorbed $CD_4$. In contrast, the 17 and 19 amu traces exhibit negligible intensity in the low temperature peak, while the 17, 18, 19 and 20 amu TPRS traces all exhibit a peak centered at ~530 K. Notably, the $H_2O$, HDO and $D_2O$ also contribute to the 17 to 20 amu TPRS features observed above ~400 K, and that methane desorption generates the distinct feature centered at 530 K. These results demonstrate that only $CD_4$ desorbs in the TPRS peak near 130 K, whereas $CD_4$ as well as $CD_3H$ desorb in the peak at 530 K, thus supporting the assignment of the low and high temperature TPRS peaks to molecularly-adsorbed methane vs. the recombination of adsorbed methyl groups and H-atoms.

Quantitative Accuracy of the DFT Results

Comparison with the experimental data shows that DFT-D3 overestimates the binding of the $CH_4$ σ-complex on $IrO_2(110)$. In contrast, it was previously found that DFT-D3 quantitatively reproduces the binding energies and apparent reaction barriers of light alkanes on the PdO(101) and $RuO2(110)$ surfaces (11, 12, 19, 20). Because methane experiences dispersion interactions with the $IrO_2(110)$ surface and yet such interactions are omitted from DFT-PBE, it is concluded here that the good quantitative agreement between the energies determined from experiment and DFT-PBE calculations is coincidental and that the DFT-PBE calculations actually overestimate the binding energy resulting from the covalent dative bonding between the $CH_4$ molecule and the $IrO_2(110)$ surface. Recent DFT calculations using the optB88-vdw functional also overestimate the $CH_4$ binding energies on $IrO_2(110)$ (18), by a similar amount as the DFT-D3 calculations. The adsorption energy of $CH_4$ on $IrO_2(110)$ for several functionals has been tested, including the hybrid HSE06 and PBE0 functionals and also functionals that incorporate dispersion (see results summarized in Table 1).

TABLE 1

$E_{ads}$ (kJ/mol) for $CH_4$ on $IrO_2(110)$ using various XC functionals with and without dispersion. Values given in parentheses include zero point corrections.

| | XC functionals without dispersion | | | | |
|---|---|---|---|---|---|
| Functional | PBE | RPBE | revPBE | Static HSE06 | Static PBE0 |
| $E_{ads}$ (kJ/mol) | 39.6 (35.7) | 11.6 (6.3) | 13.5 | 37.6 | 45.3 |

| | XC functionals with dispersion | | | | |
|---|---|---|---|---|---|
| Functional | PBE-D3 | TS | optPBE-vdw | optB88-vdw | opt86b-vdw | DF2-vdw |
| $E_{ads}$ (kJ/mol) | 70.4 | 67.5 | 64.6 | 72.4 | 78.1 | 48.2 (43.5) |

The RPBE and revPBE functionals underestimate the $CH_4$ binding energy on $IrO_2(110)$ by 20-25 kJ/mol in comparison to PBE, and similar findings have been reported for several other molecules (38). It is clear that while the RPBE functional has been reported to be more accurate for some small molecules on metal surfaces, it fails to capture the strong contribution to the σ-bonding for $CH_4$ on $IrO_2(110)$. For the hybrid-functional DFT calculations, only static single point calculations using the adsorption configuration from DFT-PBE were performed. The hybrid functionals do not dramatically change the adsorption energy in comparison to the PBE functional and full relaxation will lead to more strongly-bound $CH_4$ than found with PBE. All of the XC functionals with dispersion give similar results to PBE-D3, reinforcing the observation above that the dispersion contributions are being captured accurately. The one exception to this finding is the DF2-vdw functional, which incorporates dispersion into the revPBE family of functionals (39). Because the revPBE functional underestimates adsorption energy, the inclusion of dispersion results in an adsorption energy closer to the experimental value (and DFT-PBE with no dispersion). However, this agreement is likely fortuitous and the DF2-vdw functional is not accurately capturing the σ-bonding in this system. To test the DF2-vdw functional further, a NEB calculation was performed using this functional and find a ZPC-value of 54.9 kJ/mol for the C—H bond cleavage barrier. Combined with the ZPC $E_{ads}$ value of 43.5 kJ/mol, this results in a positive apparent barrier of 11.4 kJ/mol, conflicting with the experimental result. The source of this overestimation of the barrier to C—H bond activation is likely due to the failure of the revPBE functional to capture the σ-bonding, which leads to back-donation charge transfer that weakens the C—H bond and facilitates C—H activation.

REFERENCES

1. R. Horn, R. Schlogl, Methane activation by heterogeneous catalysis. *Catal. Lett.* 145, 23-39 (2015).
2. W. Taifan, J. Baltrusaitis, $CH_4$ conversion to value added products: Potential, limitations and extensions of a single step heterogeneous catalysis. *Appl. Catal., B* 198, 525-547 (2016).
3. J. F. Weaver, A. F. Carlsson, R. J. Madix, The adsorption and reaction of low molecular weight alkanes on metallic single crystal surfaces. *Surf. Sci. Rep.* 50, 107-199 (2003).
4. T. S. Wittrig, P. D. Szuromi, W. H. Weinberg, The interaction of ethane, propane, isobutane, and neopentane with the (110) surface of iridium. *J. Chem. Phys.* 76, 3305-3315 (1982).

5. P. D. Szuromi, J. R. Engstrom, W. H. Weinberg, Adsorption and reaction of n-alkanes on the Pt(110)–(1×2) surface. *J. Phys. Chem.* 89, 2497-2502 (1985).
6. C. B. Mullins, W. H. Weinberg, Trapping-mediated dissociative chemisorption of ethane on Ir(110)–(1×2). *J. Chem. Phys.* 92, 4508-4512 (1990).
7. A. V. Hamza, H. P. Steinruck, R. J. Madix, The dynamics of the dissociative adsorption of alkanes on Ir(110). *J. Chem. Phys.* 86, 6506-6514 (1987).
8. C. T. Campbell, J. R. V. Sellers, Enthalpies and entropies of adsorption on well-defined oxide surfaces: Experimental measurements. *Chem. Rev.* 113, 4106-4135 (2013).
9. E. W. McFarland, H. Metiu, Catalysis by doped oxides. *Chem. Rev.* 113, 4391-4427 (2013).
10. L. Chen, R. S. Smith, B. D. Kay, Z. Dohnalek, Adsorption of small hydrocarbons on rutile $TiO_2$(110). *Surf. Sci.* 650, 83-92 (2016).
11. J. F. Weaver, C. Hakanoglu, A. Antony, A. Asthagiri, Alkane activation on crystalline metal oxide surfaces. *Chem. Soc. Rev.* 43, 7536-7547 (2014).
12. J. F. Weaver, Surface chemistry of late transition metal oxides. *Chem. Rev.* 113, 4164-4215 (2013).
13. F. Zhang, L. Pan, J. Choi, V. Mehar, J. T. Diulus, A. Asthagiri, J. F. Weaver, Propane sigma-complexes on PdO(101): Spectroscopic evidence of the selective coordination and activation of primary C—H bonds. *Angew. Chem., Int. Ed.* 54, 13907-13911 (2015).
14. C. Hall, R. N. Perutz, Transition metal alkane complexes. *Chem. Rev.* 96, 3125-3146 (1996).
15. N. M. Martin, M. van den Bossche, A. Hellman, H. Gronbeck, C. Hakanoglu, J. Gustafson, S. Blomberg, N. Johanson, Z. Liu, S. Axnanda, J. F. Weaver, E. Lundgren, Intrinsic ligand effect governing the catalytic activity of Pd oxide thin films. *ACS Catal.* 4, 3330-3334 (2014).
16. C. C. Wang, S. S. Siao, J. C. Jiang, C—H bond activation of methane via sigma-d interaction on the $IrO_2$(110) surface: Density functional theory study. *J. Phys. Chem. C* 116, 6367-6370 (2012).
17. A. Antony, PhD Dissertation, University of Florida, Gainesville, Fla. (2013).
18. T. L. M. Pham, E. G. Leggesse, J. C. Jiang, Ethylene formation by methane dehydrogenation and C—C coupling reaction on a stoichiometric $IrO_2$ (110) surface—a density functional theory investigation. *Catal. Sci. Technol.* 5, 4064-4071 (2015).
19. T. Li, M. Kim, R. Rai, Z. Liang, A. Asthagiri, J. F. Weaver, Adsorption of alkanes on stoichiometric and oxygen-rich RuO2(110). *Phys. Chem. Chem. Phys.* 18, 22647-22660 (2016).
20. T. Li, R. Rai, Z. Liang, M. Kim, A. Asthagiri, J. F. Weaver, Adsorption and Oxidation of n-Butane on the Stoichiometric RuO2(110) Surface. *J. Phys. Chem. C* 120, 9863-9873 (2016).
21. B. A. Arndtsen, R. G. Bergman, Unusually mild and selective hydrocarbon C—H bond activation with positively charged iridium(III) complexes. *Science* 270, 1970-1973 (1995).
22. C. T. Reeves, D. C. Seets, C. B. Mullins, Low translational energy mechanisms in the dissociative chemisorption of methane on iridium and platinum surfaces. *J. Mol. Catal. A: Chem.* 167, 207-215 (2001).
23. Y. B. He, A. Stierle, W. X. Li, A. Farkas, N. Kasper, H. Over, Oxidation of Ir(111): From O—Ir—O trilayer to bulk oxide formation. *J. Phys. Chem. C* 112, 11946-11953 (2008).
24. W. H. Chung, D. S. Tsai, L. J. Fan, Y. W. Yang, Y. S. Huang, Surface oxides of Ir(111) prepared by gas-phase oxygen atoms. *Surf. Sci.* 606, 1965-1971 (2012).
25. R. Rai, T. Li, Z. Liang, M. Kim, A. Asthagiri, J. F. Weaver, Growth and termination of an $IrO_2$(100) film on Ir(111). *Surf. Sci.* 252, 213-221 (2016).
26. C. T. Rettner, E. K. Schweizer, H. Stein, D. J. Auerbach, Role of surface-temperature in the precursor-mediated dissociative chemisorption of $N_2$ on W(100). *Phys. Rev. Lett.* 61, 986-989 (1988).
27. S. Grimme, J. Antony, S. Ehrlich, H. Krieg, A consistent and accurate ab initio parametrization of density functional dispersion correction (DFT-D) for the 94 elements H—Pu. *J. Chem. Phys.* 132, 154104 (2010).
28. K. Anic, A. V. Bukhtiyarov, H. Li, C. Rameshan, G. Rupprechter, CO adsorption on reconstructed Ir(100) surfaces from UHV to mbar pressure: A LEED, TPD, and PM-IRAS study. *J. Phys. Chem. C* 120, 10838-10848 (2016).
29. G. Kisters, J. G. Chen, S. Lehwald, H. Ibach, Adsorption of CO on the unreconstructed and reconstructed Ir(100) surface. *Surf. Sci.* 245, 65-71 (1991).
30. T. J. Lerotholi, G. Held, D. A. King, Phase mixing and phase separation accompanying the catalytic oxidation of CO on Ir(100). *Surf. Sci.* 601, 1285-1295 (2007).
31. P. E. Blochl, Projector augmented-wave method. *Phys. Rev. B* 50, 17953-17979 (1994).
32. G. Kresse, J. Hafner, Ab initio Hellmann-Feynman molecular dynamics for liquid metals. *J. Non-Cryst. Solids* 156, 956-960 (1993).
33. G. Kresse, Ab initio molecular dynamics for liquid metals. *J. Non-Cryst. Solids* 193, 222-229 (1995).
34. J. P. Perdew, K. Burke, M. Ernzerhof, Generalized gradient approximation made simple. *Phys. Rev. Lett.* 77, 3865-3868 (1996).
35. G. Henkelman, B. P. Uberuaga, H. Jónsson, A climbing image nudged elastic band method for finding saddle points and minimum energy paths. *J. Chem. Phys.* 113, 9901-9904 (2000).
36. H. Over, Surface chemistry of ruthenium dioxide in heterogeneous catalysis and electrocatalysis: From fundamental to applied research. *Chem. Rev.* 112, 3356-3426 (2012).
37. A. Lobo, H. Conrad, Interaction of $H_2O$ with the $RuO_2$(110) surface studied by HREELS and TDS. *Surf. Sci.* 523, 279-286 (2003).
38. B. Hammer, L. B. Hansen, J. K. Norskov, Improved adsorption energetics within density-functional theory using revised Perdew-Burke-Ernzerhof functionals. *Phys. Rev. B* 59, 7413-7421 (1999).
39. K. Lee, E. D. Murray, L. Z. Kong, B. I. Lundqvist, D. C. Langreth, Higher-accuracy van der Waals density functional. *Phys. Rev. B* 82, (2010).
40. S. Gautier, S. N. Steinmann, C. Michel, P. Fleurat-Lessard, P. Sautet, Molecular adsorption at Pt(111). How accurate are DFT functionals? *Phys. Chem. Chem. Phys.* 17, 28921-28930 (2015).
41. K. Momma, F. Izumi, VESTA 3 for three-dimensional visualization of crystal, volumetric and morphology data. *J. Appl. Crystallogr.* 44, 1272-1276 (2011).

Ratios, concentrations, amounts, and other numerical data may be expressed in a range format. It is to be understood that such a range format is used for convenience and brevity, and should be interpreted in a flexible manner to include not only the numerical values explicitly recited as the limits of the range, but also to include all the individual numerical values or sub-ranges encompassed within that range as if each numerical value and sub-range is explicitly recited. To illustrate, a concentration range of "about 0.1% to about 5%" should be interpreted to include not only the explicitly recited concentration of about 0.1% to about 5%, but also include individual concentrations (e.g., 1%, 2%, 3%, and 4%) and the sub-ranges (e.g., 0.5%, 1.1%, 2.2%, 3.3%, and 4.4%) within the indicated range. In an embodiment, the term "about" can include traditional rounding according to significant figure of the numerical value. In addition, the phrase "about 'x' to 'y'" includes "about 'x' to about 'y'".

Unless defined otherwise, all technical and scientific terms used have the same meaning as commonly understood by one of ordinary skill in the art to which this disclosure belongs. Although any methods and materials similar or equivalent to those described can also be used in the practice or testing of the present disclosure, the preferred methods and materials are now described.

Embodiments of the present disclosure will employ, unless otherwise indicated, techniques of separating, testing, and constructing materials, which are within the skill of the art. Such techniques are explained fully in the literature.

It should be emphasized that the above-described embodiments are merely examples of possible implementations. Many variations and modifications may be made to the above-described embodiments without departing from the principles of the present disclosure. All such modifications and variations are intended to be included herein within the scope of this disclosure and protected by the following claims.

At least the following is claimed:

1. A catalyst comprising:
   a $IrO_2(110)$ substrate having a rutile $IrO_2(110)$ surface having exposed cus-Ir atom sites.

2. The catalyst of claim 1, wherein a stoichiometric termination of rutile $IrO_2(110)$ has a rectangular unit cell with dimensions of 3.16×6.36 Å with corresponding lattice vectors aligned along [001] and [110] crystallographic directions, respectively.

3. The catalyst of claim 1, wherein $IrO_2(110)$ surface has rows of cus-Ir atoms separated by rows of bridging-O atoms that run parallel to a [001] direction.

4. The catalyst of claim 3, wherein cus-Ir atoms and bridging-O atoms each lack a bonding partner compared with a bulk $IrO_2$ surface, wherein the lack of a bonding partner exposes single coordination vacancies.

5. The catalyst of claim 2, wherein each $IrO_2(110)$ unit cell has an areal density of cus-Ir atoms and bridging-O atoms that each equal about 34 to 40% of a surface atom density of an Ir(100) surface.

6. The catalyst of claim 2, wherein each $IrO_2(110)$ unit cell has an areal density of cus-Ir atoms and bridging-O atoms that each equal 37% of a surface atom density of an Ir(100) surface.

7. A method of making an $IrO_2(110)$ surface, comprising:
   oxidizing Ir(100) substrate at about 725 to 875 K and a $O_2$ partial pressure of about 0.5 to 100 Torr;
   evacuating $O_2$ from the chamber until the pressure reaches less than $10^{-7}$ Torr with the sample held at 600 to 650 K; and
   forming a rutile $IrO_2(110)$ surface having exposed cus-Ir atom sites.

8. A method of making a product from $CH_4$, comprising:
   exposing a catalyst comprising an $IrO_2$ substrate having a rutile $IrO_2(110)$ surface having exposed cus-Ir atom sites and a $CH_4$ gas to one another; and
   forming one or more products.

9. The method of claim 8, wherein the product is selected from the group consisting of: $CH_3OH$, $CH_2O_1$, $C_2H_4$, and a combination thereof.

10. A system of activating $CH_4$, comprising:
    a first device for introducing $CH_4$ to a catalyst comprising an $IrO_2$ substrate having a rutile $IrO_2(110)$ surface having exposed cus-Ir atom sites;
    a second device for collecting one or more products of the catalytic reaction of $CH_4$.

11. The system of claim 10, wherein the $CH_4$ is introduced to the substrate at about 150 to 300 K.

12. The system of claim 10, wherein the product is selected from the group consisting of: $CH_3OH$, $CH_2O$, $C_2H_4$, and a combination thereof.

13. The system of claim 10, wherein a stoichiometric termination of rutile $IrO_2(110)$ has a rectangular unit cell with dimensions of 3.16×6.36 Å with corresponding lattice vectors aligned along [001] and [110] crystallographic directions, respectively.

14. The system of claim 10, wherein $IrO_2(110)$ surface has rows of cus-Ir atoms separated by rows of bridging-O atoms that run parallel to a [001] direction.

15. The system of claim 14, wherein cus-Ir atoms and bridging-O atoms each lack a bonding partner compared with a bulk $IrO_2$ surface, wherein the lack of a bonding partner exposes single coordination vacancies.

16. The system of claim 13, wherein each $IrO_2(110)$ unit cell has an areal density of cus-Ir atoms and bridging-O atoms that each equal 37% of a surface atom density of an Ir(100) surface.

* * * * *